(12) United States Patent
Miklatzky et al.

(10) Patent No.: US 10,302,495 B2
(45) Date of Patent: May 28, 2019

(54) HAIR READER, DISPENSER DEVICE AND RELATED SYSTEMS AND METHODS

(71) Applicant: COLORIGHT LTD., Rehovot (IL)

(72) Inventors: Efraim Miklatzky, Neve Ilan (IL); Daniel Mandelik, Rehovot (IL); Gilad Davara, Rehovot (IL); Eliyahu Benny, Rishon-LeZion (IL); Oded Livneh, Holon (IL); Elena Ishkov, Givataim (IL); Uri Zadok, Herzliya (IL); Lior Shahar, Kiryat-Ono (IL)

(73) Assignee: ColoRight Ltd., Rehovot (IL)

( * ) Notice: Subject to any disclaimer, the term of this patent is extended or adjusted under 35 U.S.C. 154(b) by 0 days.

(21) Appl. No.: 15/023,398

(22) PCT Filed: Sep. 28, 2014

(86) PCT No.: PCT/IL2014/050850
§ 371 (c)(1),
(2) Date: Mar. 20, 2016

(87) PCT Pub. No.: WO2015/044944
PCT Pub. Date: Apr. 2, 2015

(65) Prior Publication Data
US 2016/0209272 A1    Jul. 21, 2016

Related U.S. Application Data

(60) Provisional application No. 61/883,263, filed on Sep. 27, 2013, provisional application No. 61/926,909, (Continued)

(30) Foreign Application Priority Data

Sep. 26, 2013  (CA) ...................................... 2828363
Sep. 24, 2014  (WO) .................. PCT/IB2014/064809

(51) Int. Cl.
*G01J 3/46* (2006.01)
*G01N 21/25* (2006.01)
(Continued)

(52) U.S. Cl.
CPC ............ *G01J 3/462* (2013.01); *A45D 44/005* (2013.01); *B01F 13/1055* (2013.01);
(Continued)

(58) Field of Classification Search
CPC .... G01J 3/462; G01J 3/463; G01J 3/50; G01J 3/0272; A45D 44/005; B01F 13/1055;
(Continued)

(56) References Cited

U.S. PATENT DOCUMENTS 4,643,313 A    2/1987   Robson
5,205,837 A    4/1993   Andrean et al.
(Continued)

FOREIGN PATENT DOCUMENTS

CA    2828363 A1    3/2015
DE    3609962 A1    6/1987
(Continued)

OTHER PUBLICATIONS

Birngruber C et al: The color(s) of human hair-Forensic hair analysis with SpectraCube; vol. 185, No. 1-3, Mar. 10, 2009, pp. e19-e23; Forensic Science International, Elsevier Scientific Publishers Ireland Ltd, IE; available online Jan. 24, 2009.
(Continued)

*Primary Examiner* — Michael Collins
(74) *Attorney, Agent, or Firm* — Oblon, McClelland, Maier & Neustadt, L.L.P.

(57) ABSTRACT

The present disclosure relates to hair readers, dispenser devices, and related systems and methods. For example the present application relates to a method of optically acquiring data from keratinous fibers, the method comprising: a.
(Continued)

illuminating the keratinous fibers such that light reflected and/or deflected and/or transmitted by the fibers is incident upon a detector and converted into electrical signals by the detector; and b. computing, from electrical signals, a plurality of spectra of the keratinous fibers such that each spectrum of the plurality of spectra respectively corresponds to (i) a different respective portion of the keratinous fibers and/or (ii) material within a different sub-region of space within which at least a portion of the keratinous fibers are disposed.

11 Claims, 24 Drawing Sheets

Related U.S. Application Data filed on Jan. 13, 2014, provisional application No. 61/984,798, filed on Apr. 27, 2014, provisional application No. 61/984,861, filed on Apr. 27, 2014, provisional application No. 61/985,331, filed on Apr. 28, 2014.

(51) Int. Cl.

| | | |
|---|---|---|
| *A45D 44/00* | (2006.01) | |
| *B01F 13/10* | (2006.01) | |
| *G01J 3/50* | (2006.01) | |
| *G01J 3/02* | (2006.01) | |
| *G01N 21/31* | (2006.01) | |
| *G01N 21/84* | (2006.01) | |

(52) U.S. Cl.
CPC ........ *B01F 13/1063* (2013.01); *G01J 3/0272* (2013.01); *G01J 3/463* (2013.01); *G01J 3/50* (2013.01); *G01N 21/25* (2013.01); *G01N 21/251* (2013.01); *G01N 21/31* (2013.01); *G01N 2021/8444* (2013.01)

(58) Field of Classification Search
CPC .... B01F 13/1063; G01N 21/31; G01N 21/25; G01N 21/251; G01N 2021/8444
USPC .................................................. 700/231–244
See application file for complete search history.

(56) References Cited

U.S. PATENT DOCUMENTS

| | | | |
|---|---|---|---|
| 5,660,342 A | 8/1997 | Bock | |
| 5,754,283 A | 5/1998 | Keane et al. | |
| 5,851,181 A | 12/1998 | Talmor | |
| 5,990,058 A | 11/1999 | Bac et al. | |
| 6,096,359 A | 8/2000 | Bombardelli et al. | |
| 6,170,980 B1 | 1/2001 | Martin | |
| 6,248,749 B1 | 6/2001 | Demarchez et al. | |
| 6,330,341 B1 | 12/2001 | MacFarlane et al. | |
| 6,362,885 B1 | 3/2002 | Osumi et al. | |
| 6,440,175 B1* | 8/2002 | Stanley, III ............ A45D 19/02 206/568 |
| 6,529,446 B1 | 3/2003 | De | |
| 6,547,833 B2 | 4/2003 | Casperson et al. | |
| 6,613,311 B2 | 9/2003 | Imperial | |
| 6,707,929 B2 | 3/2004 | Marapane et al. | |
| 6,764,523 B2 | 7/2004 | Casperson et al. | |
| 6,790,240 B2 | 9/2004 | Schulze et al. | |
| 6,807,297 B1 | 10/2004 | Tankovich et al. | |
| 6,818,022 B2 | 11/2004 | Massoni | |
| 6,984,377 B2 | 1/2006 | Witham et al. | |
| 7,110,117 B2 | 9/2006 | Grossinger et al. | |
| 7,204,856 B2 | 4/2007 | Schulze et al. | |
| 7,304,739 B2 | 12/2007 | Grossinger et al. | |
| 7,458,992 B2 | 12/2008 | Schmenger et al. | |
| 7,463,356 B2 | 12/2008 | Grossinger et al. | |
| 7,508,508 B2 | 3/2009 | Grossinger et al. | |
| 7,523,018 B2 | 4/2009 | Grossinger et al. | |
| 7,708,021 B2 | 5/2010 | Ghannad et al. | |
| 9,205,283 B2* | 12/2015 | Miklatzky .............. A45D 19/02 |
| 9,844,687 B2* | 12/2017 | Landa ..................... A45D 19/02 |
| 9,949,545 B2* | 4/2018 | Grez ..................... A45D 19/00 |
| 2001/0002025 A1 | 5/2001 | Rolf-Dieter et al. | |
| 2002/0010556 A1 | 1/2002 | Marapane et al. | |
| 2002/0157191 A1 | 10/2002 | Casperson et al. | |
| 2002/0194684 A1 | 12/2002 | Wiesche et al. | |
| 2003/0028978 A1 | 2/2003 | Schulze et al. | |
| 2004/0000015 A1 | 1/2004 | Grossinger et al. | |
| 2004/0013616 A1 | 1/2004 | Witham et al. | |
| 2005/0015895 A1 | 1/2005 | Azizova et al. | |
| 2005/0019398 A1 | 1/2005 | Kotharl et al. | |
| 2005/0036677 A1 | 2/2005 | Ladjevardi | |
| 2005/0039271 A1 | 2/2005 | Schulze et al. | |
| 2005/0165705 A1 | 7/2005 | Lauper et al. | |
| 2005/0177032 A1 | 8/2005 | Grossinger et al. | |
| 2005/0244343 A1 | 11/2005 | Witham et al. | |
| 2006/0149151 A1 | 7/2006 | Ladjevardi et al. | |
| 2006/0195300 A1 | 8/2006 | Grossinger et al. | |
| 2007/0159290 A1 | 7/2007 | Grossinger et al. | |
| 2007/0265867 A1 | 11/2007 | Lin | |
| 2008/0013077 A1 | 1/2008 | Orelli et al. | |
| 2008/0068604 A1 | 3/2008 | Grossinger et al. | |
| 2008/0256724 A1 | 10/2008 | Bolton et al. | |
| 2009/0119852 A1 | 5/2009 | Marsh | |
| 2011/0038818 A1 | 2/2011 | Onyebuagu et al. | |
| 2012/0320191 A1 | 12/2012 | Meschkat et al. | |
| 2014/0082854 A1 | 3/2014 | Landa et al. | |

FOREIGN PATENT DOCUMENTS

| | | |
|---|---|---|
| DE | 4205112 A1 | 8/1993 |
| DE | 10260880 A1 | 7/2004 |
| DE | 102006008149 A1 | 8/2007 |
| EP | 0590538 A1 | 4/1994 |
| EP | 1817976 A1 | 8/2007 |
| EP | 2081668 A1 | 7/2009 |
| EP | 2133673 A1 | 12/2009 |
| EP | 2193781 A1 | 6/2010 |
| FR | 2402446 A1 | 4/1979 |
| FR | 2532174 A1 | 3/1984 |
| FR | 2901131 A1 | 11/2007 |
| JP | 2000116622 A | 4/2000 |
| JP | 2004198398 A | 7/2004 |
| JP | 2004212088 A | 7/2004 |
| JP | 2007212140 A | 8/2007 |
| JP | 2008285429 A | 11/2008 |
| KR | 100802645 A | 9/2004 |
| KR | 20040076861 A | 9/2004 |
| WO | 0145647 A2 | 6/2001 |
| WO | 02083282 A1 | 10/2002 |
| WO | 03012728 A1 | 2/2003 |
| WO | 03074015 A1 | 9/2003 |
| WO | 2004058202 A1 | 7/2004 |
| WO | 2004082650 A1 | 9/2004 |
| WO | 2004101689 A2 | 11/2004 |
| WO | 2008046518 A1 | 4/2008 |
| WO | 2009121643 A2 | 10/2009 |
| WO | 2009152033 A1 | 12/2009 |
| WO | 2010004565 A2 | 1/2010 |
| WO | 2010060601 A1 | 6/2010 |
| WO | 2010100231 A1 | 9/2010 |
| WO | 11003554 A2 | 1/2011 |
| WO | 2012032671 A1 | 3/2012 |
| WO | 2012127429 A1 | 9/2012 |

OTHER PUBLICATIONS

WO 2008046518 Machine Translation (by EPO and Google); published on Apr. 24, 2008 Beiersdorf AG et al.
DE 10260880 Machine Translation (by EPO and Google); published on Jul. 1, 2004, Henkel KGAA.
DE 3609962 Machine Translation (by EPO and Google); published on Jun. 19, 1987, Panke Hartmut.

(56) References Cited

OTHER PUBLICATIONS

DE 4205112 Machine Translation (by EPO and Google); published on Aug. 26, 1993, Brackmann Hans Peter DR Med.
EP 2081668 Machine Translation (by EPO and Google); published on Jul. 29, 2009, Beiersdorf AG.
WO 2009121643 Machine Translation (by EPO and Google); published on Oct. 8, 2009, Henkel AG & CO KGAA et al.
FR 2402446 Machine Translation (by EPO and Google); published on Apr. 6, 1979, Oreal.
FR 2532174 Machine Translation (by EPO and Google); published on Mar. 2, 1984, Bristol Myers Co.
FR 2901131 Machine Translation (by EPO and Google); published on Nov. 23, 2007, Oreal.
International Search Report for PCT/IB2015/000724; search report dated Nov. 16, 2015.
International Search Report for PCT/IB2015/053065; search report dated Sep. 1, 2015.
International Search Report for PCT/IL2014/50850; search report dated Mar. 23, 2015.
JP 2000116622 Machine Translation (by EPO and Google); published on Apr. 25, 2000, Kose Corp.
JP 2004198398 Machine Translation (by EPO and Google); published on Jul. 15, 2004, Kose Corp.
JP 2004212088 Machine Translation (by EPO and Google); published on Jul. 29, 2004, Kose Corp.
JP 2007212140 Machine Translation (by EPO and Google); published on Aug. 23, 2007, Kose Corp.
JP 2008285429 Machine Translation (by EPO and Google); published on Nov. 27, 2008, Shiseido Co Ltd.
KR100802645 Machine Translation (by EPO and Google); published on Sep. 3, 2004.
KR20040076861 Machine Translation (by EPO and Google); published on Sep. 3, 2004.
WO 0145647 Machine Translation (by EPO and Google); published on Jun. 28, 2001, Henkel KGAA et al.
WO 03074015 Machine Translation (by EPO and Google); published on Sep. 12, 2003, Henkel KGAA et al.
WO 2004082650 Machine Translation (by EPO and Google); published on Sep. 3, 2004, Henkel KGAA et al.
Written Opinion for PCT/IB2015/000724; written opinion dated Nov. 16, 2015.
Written Opinion for PCT/IB2015/053065; written opinion dated Sep. 1, 2015.
Written Opinion for PCT/IL2014/50850; written opinion dated Mar. 23, 2015.
DE 102006008149 Machine Translation (by EPO and Google); published on Aug. 23, 2007, Henkel KGAA.
Office Action dated Jul. 3, 2018 in Japanese Patent Application No. 2016-516935 (with unedited computer generated English translation), 12 pages.
Office Action dated May 22, 2018 in corresponding European Patent Application No. 14 799 553.4, 5 pages.

* cited by examiner

Legend

— · · — Generic Hair strand (no color information) – top view

▭ White hair strand – top view

▬ Black hair strand – top view

▨ Grey hair strand – top view

⬢ Generic Hair strand (no color information) – cross-section view

○ White hair strand – cross section view

● Black hair strand – cross section view

◉ Grey hair strand – cross section view

FIG. 5

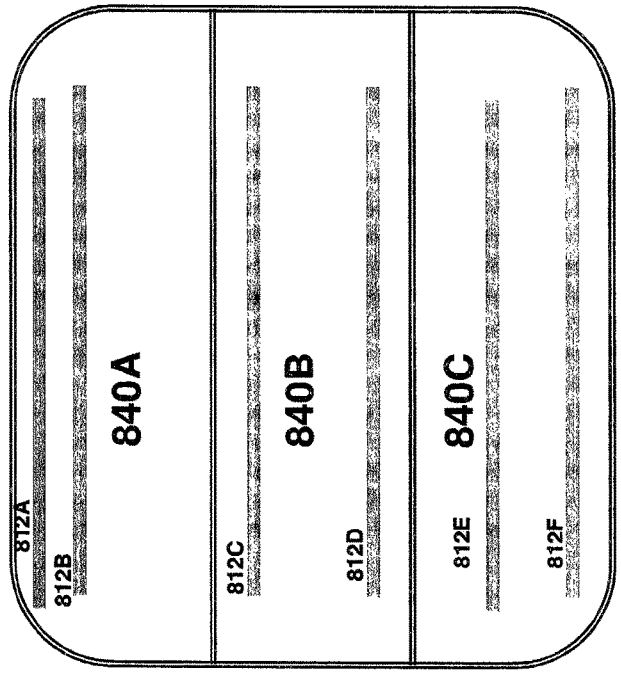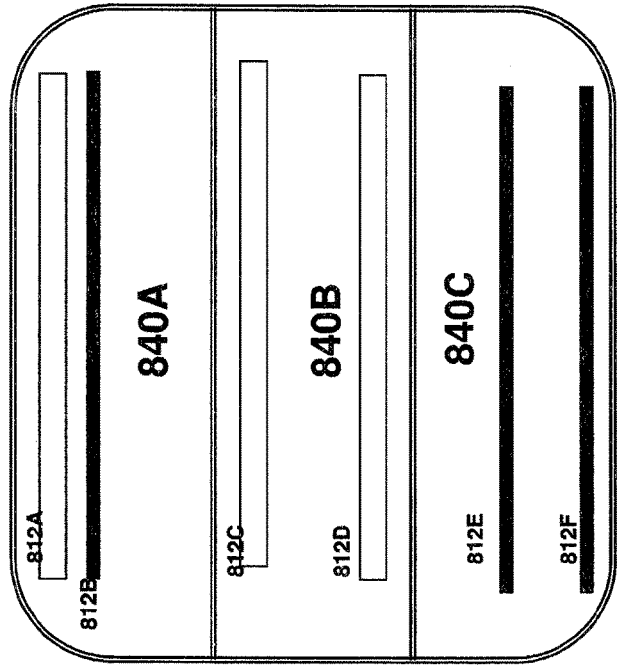
FIG. 10 ously-acquired data. In some embodiments, a customized hair-coloring coloring composition is prepared according to optically-detected property(ies) of the hair.
HAIR READER, DISPENSER DEVICE AND RELATED SYSTEMS AND METHODS

CROSS-REFERENCE TO RELATED APPLICATIONS

The present application claims priority to CA 2,828,363 filed Sep. 26, 2013, U.S. 61/883,263 filed Sep. 27, 2014; U.S. 61/926,909 filed Jan. 13, 2014 and U.S. 61/984,798 filed Apr. 27, 2014, and PCT/IB2014/064809 filed Sep. 24, 2014, all of which are incorporated by reference in their entirety.

BACKGROUND AND RELATED ART

The following issued patents and patent publications provide potentially relevant background material, and are all incorporated by reference in their entirety: U.S. Pat. Nos. 4,643,313, 5,205,837, 5,660,342, 5,754,283, 5,851,181, 5,990,058, 6,096,359, 6,170,980, 6,248,749, 6,362,885, 6,529,446, 6,547,833, 6,613,311, 6,707,929, 6,764,523, 6,790,240, 6,818,022, 6,984,377, 7,110,117, 7,204,856, 7,304,739, 7,458,992, 7,463,356, 7,508,508, 7,523,018, 7,708,021, US 20010002025, US 20020010556, US 20020157191, US 20020194684, US 20030028978, US 20040000015, US 20040013616, US 20050015895, US 20050019398, US 20050039271, US 20050165705, US 20050177032, US 20050244343, US 20060149151, US 20060195300, US 20070159290, US 20070265867, US 20080013077, US 20080068604, US 20080256724, US 20090119852, US 20110038818, DE 10260880, DE 2006008149, DE 3609962, DE 4205112, EP 0590538, EP 1817976, EP 2081668, EP 2193781, FR 2402446, FR 2532174, FR 2901131, JP 2000116622, JP 2004198398, JP 2004212088, JP 2007212140, JP 2008285429, KR100802645, KR20040076861, WO 0145647, WO 02083282, WO 03012728, WO 03074015, WO 04101689, WO 11003554, WO 2004058202, WO 2004082650, WO 2004101689, WO 2008046518, WO 2009121643, WO 2009152033, WO 2010004565, WO 2010060601, WO 2010100231, WO 2012032671,

SUMMARY

Some embodiments of the present invention relate to hair-reader devices for optically acquiring data from human hair or from other keratinous fibers. In some embodiments, one or more physical and/or chemical properties of the hair are computed from the optically-acquired data. In some embodiments, a customized hair-coloring coloring composition is prepared according to optically-detected property(ies) of the hair.

Some embodiments of the present invention relate to dispenser systems for oxidative hair-coloring. A plurality of containers are engaged to a dispenser such that some of the containers contain dye precursor and are substantially free of coupler while other containers contain coupler and are substantially free of dye precursor. The dispenser is configured to dispense contents of the containers to provide multi-container combinations. The dispenser system may be used with any presently-disclosed hair-reader device, or with any other hair-reader device, or in any other context.

Some embodiments of the present invention relate to dispensing of cosmetic agents (e.g. for hair-coloring or for any other cosmetic application) where for each container, data describing physical and/or chemical property(ies) of the cosmetic material therein is encoded on the container. This data is read by a code-reader operatively linked to a dispensing device which dispenses the cosmetic material from the containers according to the data reader from the containers.

A method related to the aforementioned hair-reader device is now disclosed. This method comprises illuminating keratinous fiber(s) and acquiring a plurality of spectra (e.g. reflection spectra) of the keratinous fiber(s) such that each spectrum of the plurality respectively corresponds to a different respective portion of the keratinous fibers.

This method may be implemented using first and second optical systems together with a two-dimensional array of photodetectors where each row of photodetectors detects a different respective spectrum (e.g. reflection spectrum).

In some embodiments, the method is useful for classifying hair. A hair-coloring composition or treatment may be computed in accordance with the reflection spectra. Hair-coloring agents (e.g. dye(s) and/or oxidizing agents and/or alkalizing agents(s)) for the preparation of the coloring composition may be dispensed in accordance with the reflection spectra. A hair-coloring system implementing such method is also disclosed.

A method of optically acquiring data from keratinous fiber(s) comprises: a. illuminating the keratinous fiber(s) such that light reflected and/or deflected and/or transmitted by the fiber(s) is incident upon a detector and converted into electrical signal(s) by the detector; and b. computing, from electrical signal(s), a plurality of spectra of the keratinous fiber(s) such that each spectrum of the plurality of spectra respectively corresponds to (i) a different respective portion of the keratinous fiber(s) and/or (ii) material within a different sub-region of space within which at least a portion of the keratinous fiber(s) are disposed.

In some embodiments, the method is performed so that i. the illuminated fiber(s) are in a first object plane; ii. a first image is formed at an intermediate location along an optical path between the fiber(s) and the detector(s), the intermediate location being configured both as a first image plane and a second object plane. the first image being an at least 1D-focused image of the fiber(s); and iii. a second image is formed at the detector, the second image being an image of the first image.

In some embodiments the method is performed so that due to a presence of at least one imaging system(s): i. the illuminated fiber(s) are in a first object plane; ii. a first image is formed at an intermediate location along an optical path between the fiber(s) and the detector(s), the intermediate location being configured both as a first image plane and a second object plane. the first image being an at least 1D-focused image of the fiber(s); and iii. a second image is formed at the detector, the second image being an image of the first image.

In some embodiments, the image system(s) are disposed along the optical path.

In some embodiments, a slit or aperture is disposed along the optical path between the keratinous fiber(s) and the detector(s) and the intermediate location substantially corresponds to the slit or aperture.

In some embodiments, the detector comprises a plurality of constitutive photodetectors arranged in a two-dimensional planar array, a plane of which corresponds to an image plane of the second image.

In some embodiments, first and second sub-sets (e.g. disjoint sub-sets) of the constitutive photodetectors respectively generate first reflection and second spectra that respectively correspond (i) to first and second portions of the keratinous fibers and/or (ii) material within a first and second subs-region of space within which at least a portion of the keratinous fiber(s) are disposed.

In some embodiments, in one direction the sub-sets of photodetectors are parallel to each other.

In some embodiments, the illuminated fibers are aligned with one another along an alignment axis and the first and second portions of the fibers corresponding to the first and second spectra are aligned with each other along the alignment axis.

In some embodiments, a first direction of the array of photodetectors corresponds to varying wavelength and a second direction perpendicular to the first direction corresponds to different portions of the keratinous fibers.

In some embodiments, each reflection spectrum of the plurality of spectra respectively corresponds to a different respective disjoint portion of the keratinous fibers.

In some embodiments, the method further comprises: c. electronically comparing a spectrum specific to a first of the portions of the keratinous fiber(s) with a spectrum specific to the second of the portions of the keratinous fiber(s); and d. in accordance with the results of the comparison, classifying the keratinous fiber(s) as homogeneous or heterogeneous with respect to color.

In some embodiments, the method further comprises: c. electronically comparing a reflection spectrum specific to a first of the portions of the keratinous fiber(s) with a reflection spectrum specific to the second of the portions of the keratinous fiber(s); and d. in accordance with the results of the comparison, classifying the keratinous fiber(s) as homogeneous or heterogeneous with respect to color.

In some embodiments, the method further comprises: c. electronically comparing a spectrum specific to a first of the portions of the keratinous fiber(s) with a spectrum specific to the second of the portions of the keratinous fiber(s); and d. dispensing a combination of hair-coloring agents according to the results of the comparing.

In some embodiments, the method further comprises: c. electronically comparing a reflection spectrum specific to a first of the portions of the keratinous fiber(s) with a reflection spectrum specific to the second of the portions of the keratinous fiber(s); and d. dispensing a combination of hair-coloring agents according to the results of the comparing.

A fiber-coloring-related method comprises: a. disposing keratinous fibers of a subject so that a different portion of the fiber(s) is respectively located in a different slice of a region of space divided into a plurality of slices; b. for each slice of the plurality, respectively acquiring spectral data specific to the respective portion of the keratinous fibers disposed within the slice; and c. electronically comparing spectral data specific to a first of the portions of the keratinous fiber(s) with spectral data specific to the second of the portions of the keratinous fiber(s).

A fiber-coloring-related method comprises: a. disposing keratinous fibers of a subject so that a different portion of the fiber(s) is respectively located in a different slice of a region of space divided into a plurality of slices; b. for each slice of the plurality, measuring a respective spectrum specific to the respective portion of the keratinous fibers disposed within the slice; and c. electronically comparing a first of the spectra descriptive of a first portion of the fiber(s) with a second of the spectra of descriptive of a second portion of the fiber(s).

In some embodiments, one or both of the first and second spectra are reflection spectra.

In some embodiments, the method is performed to compute a uniformity and/or homogeneity parameter.

In some embodiments, the uniformity and/or homogeneity parameter is a hair-strand uniformity and/or homogeneity parameter.

In some embodiments, the uniformity and/or homogeneity parameter is a color-space parameter.

In some embodiments, the color-space parameter is a LAB color-space value.

In some embodiments, the method further comprises in accordance with the results of the comparing, dispensing a combination of hair-coloring agents.

In some embodiments, the method further comprises: classifying the keratinous fiber(s) as homogeneous or heterogeneous with respect to color and/or color-space value, wherein the dispensing is performed in accordance with the results of the classifying.

In some embodiments, the method further comprises: classifying the keratinous fiber(s) as homogeneous or heterogeneous with respect to color and/or color-space value.

A method of coloring keratinous fibers comprises: a. disposing keratinous fibers of a subject so that a different fiber(s) sub-population is respectively located in each slice of a region of space divided into a plurality of slices; b. for each of the slices, respectively acquiring spectral data specific to the respective sub-population of the keratinous fibers disposed within the slice; c. electronically comparing spectral data specific to a first of the sub-populations with spectral data specific to the second of the sub-populations; and d. computing a parameter related to hair homogeneity in accordance with the results of the electronic comparing.

In some embodiments, (i) the method further comprises: e. in accordance with the comparing of the spectral data, electronically classifying the keratinous fibers as natural-grey hair or as artificially colored grey hair; and the dispensing is performed in accordance with the results of the classifying.

In some embodiments, the image is anisotropically magnified at different magnification values in orthogonal axes in the image plane—i.e. a first magnification value which may be equal to one or to any other value; i.e. a second magnification value which is different from the first t magnification value in the second axis.

In some embodiments, the method is performed so that the image plane that is co-planar with the slit or aperture is an image plane containing a only-1D-focused-image that is focused in a first axis within the image plane and blurred in a second axis that is orthogonal to the first axis.

A system for acquiring spectral data from keratinous fiber(s) comprises: a. a device housing defining a fiber(s)-placement location; b. a source light configured to illuminate keratinous fiber(s) when situated at the fiber-placement location so that at least a portion of the fiber(s) is situated within a region of space; c. apparatus configured for each of the slices, to respectively acquire spectral data specific to the material disposed within each slice.

A system for acquiring spectral data from keratinous fiber(s) comprises: a. a device housing defining a fiber(s)-placement location; b. a source light configured to illuminate keratinous fiber(s) when situated at the fiber-placement location so that at least a portion of the fiber(s) is situated within a region of space; c. apparatus configured for each of the slices, to respectively acquire spectral data specific to a different portion of the keratinous fiber(s).

In some embodiments, the apparatus comprises a monochromator or spectral analyzer.

In some embodiments, the monochromator or spectral analyzer comprises at least one of a grating and a prism.

In some embodiments, a slit or aperture is disposed upon an optical path between the fiber(s) and a light detector.

A system for acquiring spectral data from keratinous fiber(s) comprises: a. a device housing defining a fiber(s)-placement location; b. a source of light configured to illuminate keratinous fibers when situated at the fiber-placement location; c. a slit or aperture or collimating lens; d. a grating and/or prism and/or other color-dispersion optics; e. a detector for detecting light; and f. first and second optical systems configured to focus light reflected and/or deflected and/or transmitted by the illuminated keratinous fibers so that: i. light reflected and/or deflected and/or transmitted by the keratinous fiber(s) is focused by the first imaging system to form an at least 1D-focused image of the keratinous fiber(s) at an intermediate location along an optical path between the fiber(s) and the detector; and ii. the grating and/or prism and/or other color-dispersion optics and the second optical system are situated on an optical path between the slit or aperture or collimating lens and the detector such that the light reflected from and/or deflected by and/or transmitted by the keratinous fibers reaches the detector via the grating and/or prism and/or other color-dispersion optics and the second optical system, wherein: A. a presence of the grating and/or prism and/or other color-dispersion optics causes the detector to detect spectral data of the keratinous fiber(s); and B. a presence of the second imaging system focuses keratinous-fiber(s)-reflected and/or deflected and/or transmitted light on the detector (e.g. on a planar array thereof) to form, on the detector, an image of the keratinous fiber(s) at the intermediate location(s). This image may be In some embodiments, the intermediate location(s) may correspond to a location of the slit (or other aperture) or to a location of the grating and/or prism and/or other color-dispersion optics.

A system for acquiring spectral data from keratinous fiber(s) comprises: a. a device housing defining a fiber(s)-placement location; b. a light source configured to illuminate keratinous fibers when situated at the fiber-placement location; c. a 2D planar array of photodetectors; and d. optical components configured to form, from light reflected and/or deflected and/or transmitted by the fiber(s): i. spectral data in a first dimension of the 2D planar array of photodetectors; and ii. an at least 1D-focused image of the keratinous fibers in a second direction of the 2D planar array of photodetectors, the second direction being perpendicular to the first direction.

In some embodiments, the slit defines an elongate axis and the keratinous fibers(s) are substantially aligned in a direction that is perpendicular to the elongate axis of the slit.

A method of optically acquiring data from keratinous fiber(s) comprises: a. illuminating the fiber(s) by light such that light reflected by the fiber(s) subsequently passes through a slit or aperture; and b. analyzing the output of photodetector(s) to (i) determine spectral data of the illuminated fiber(s) and/or (ii) calculate a hair treatment from the analyzed output, wherein the illuminated fiber(s) are in an object plane and a presence of one or more optical components on an optical path between the fiber(s) and the slit or aperture cause the formation of an image plane so that the slit or aperture is located within the image plane.

In some embodiments, the image is anisotropically magnified at different magnification values in orthogonal axes in the image plane—i.e. a first magnification value which may be equal to one or to any other value; i.e. a second magnification value which is different from the first magnification value in the second axis.

In some embodiments, the image plane that is co-planar with the slit or aperture is an image plane containing a only-1D-focused-image that is focused in a first axis within the image plane and blurred in a second axis that is within the image plane and is orthogonal to the first axis.

A method of optically acquiring data from keratinous fiber(s) comprises: a. illuminating the fiber(s) by light such that light reflected by the fiber(s) subsequently passes through a slit or aperture; and b. analyzing the output of photodetector(s) to (i) determine spectral data of the illuminated fiber(s) and/or (ii) calculate a hair treatment from the analyzed output, wherein the illuminated fiber(s) are in an object plane and a presence of one or more optical components on an optical path between the fiber(s) and the slit or aperture cause the formation first and second only-1D-focused-images on opposite sides of the slit or aperture and wherein light from both the first and second only-1D-focused-images is incident upon and detected by the photodetector(s) (e.g. to re-combine the only-1D-focused-image.

In some embodiments, the first only-1D-focused-image is focused in a first direction and blurred in a second direction orthogonal to the first direction, and the second only-1D-focused-image is focused in the second direction and blurred in the first direction.

In some embodiments, the illuminated fibers are aligned with each other.

In some embodiments, at least one of the spectrum(s), or at least a plurality of spectrum(a) are reflection spectrum(a) or absorption spectrum(a) or transmission spectrum(a).

In some embodiments, the keratinous fiber(s) are illuminated by incoherent light.

A method of optically acquiring data from keratinous fiber(s) comprises: a. illuminating the keratinous fiber(s); b. from light reflected and/or deflected and/or transmitted by the fiber(s), respectively forming first and second only-1D-focused images of the fiber(s) at first and second intermediate locations; c. passing from light of the first and second only-1D-focused images through color-dispersion optics; and d. receiving, by a light detector, light from the first and second only-1D-focused images after this light has passed through the color-dispersion optics so as to detect spectrum (a) of the keratinous fiber(s).

In some embodiments, the first and second only-1D-focused images are formed are formed by optical components comprising a toric lens.

A system for optically acquiring data from keratinous fiber(s), the system comprising: a. a source of light configured to illuminate the keratinous fiber(s); b. an imaging system configured to respectively form, from light reflected and/or deflected and/or transmitted by the fiber(s), first and second only-1D-focused images of the fiber(s) at first and second intermediate locations; c. color-dispersion optics configured to receive light of the first and second only-1D-focused images; and d. by a light detector configured to receive light from the first and second only-1D-focused images after this light has passed through the color-dispersion optics so as to detect spectrum(a) of the keratinous fiber(s).

In some embodiments, the first only-1D-image is focused in a first image-plane direction and blurred in a second image-plane direction orthogonal to the first image-plane direction and the second only-1D-image is focused in the second image-plane direction and blurred in the first image-plane direction.

In some embodiments, the keratinous fiber(s) are aligned along an alignment axis.

In some embodiments, i. the keratinous fiber(s) are aligned along an alignment axis; ii. the first only-1D-image is focused in a first image-plane direction along the alignment axis and blurred in a second image-plane direction orthogonal to the first image-plane direction; and iii. the second only-1D-image is focused in the second image-plane direction and blurred in the first image-plane direction.

In some embodiments, the first and second only-1D-focused images are recombined at the light detector.

In some embodiments, the first and second only-1D-focused images are recombined into a 2D-focused-image at the light detector.

In some embodiments, the reflected and/or deflected and/or transmitted by the fiber(s) passes through an aperture or a slit en route to the color-dispersion optics.

In some embodiments, an image plane location of the first or second only-1D-focused image corresponds to a plane of slit or the aperture.

In some embodiments, further comprising according to the detected spectrum(a), calculating a hair-treatment recipe and/or dispensing a combination of hair-coloring agents.

A system for preparing a hair-coloring composition comprises: a. a plurality of containers, each container holding a different permanent hair-coloring agent therein, a first of the plurality of containers containing dye precursor and being substantially free of coupler, a second of the plurality of containers containing coupler and being substantially free of dye precursor; and b. a dispenser configured to dispense contents of the containers to provide multi-container combinations comprising material from the first and second containers.

A system for preparing a hair-coloring composition comprising: a. a plurality of containers including first and second containers; b. a plurality of tablets disposed within each of the containers including each tablet comprising at least one of (i) permanent hair-coloring dye precursor and (ii) permanent hair-coloring dye coupler such that in first of the containers, the plurality of tablets including tablets of first and second types such that (A) tablets of the first type comprise permanent hair-coloring dye precursor and are substantially free of permanent hair-coloring dye coupler, and (B) tablets of the second type comprise permanent hair-coloring dye coupler and are substantially free of permanent hair-coloring dye precursor, a majority of tablets in the first container being of the first type, a majority of tablets in the second container being of the second type, c. a dispenser configured to dispense the tablets so as to provide multi-container tablet combinations comprising tablets of the first and second types from the first and second containers.

In some embodiments, at least a majority of tablets in the first container are of the first type, of substantially the same dye coupler and have substantially the same size.

In some embodiments, the plurality of containers comprises a third container, such that (i) at least a majority of tablets within the first container are members of TABLET_SET1 (ii) at least a majority of tablets within the third container are members of TABLET_SET3; (iii) all tablets of TABLET_SET1 are of the first type and comprise the same precursor PREC_1; (iv) all tablets of TABLET_SET3 are of the first type and comprise the same precursor PREC_1 that is the same as that of TABLET_SET3; (v) an average load (by weight) of tablets of TABLET_SET1 is $LW_1$; (v) an average load (by weight) of tablets of TABLET_SET3 is $LW_3$; (vi) and a ratio between $LW_1$ and $LW_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 10.

In some embodiments, the plurality of containers comprises a third container, such that (i) at least a majority of tablets within the first container are members of TABLET_SET1 (ii) at least a majority of tablets within the third container are members of TABLET_SET3; (iii) all tablets of TABLET_SET1 are of the first type and comprise the same precursor PREC_1; (iv) all tablets of TABLET_SET3 are of the first type and comprise the same precursor PREC_1 that is the same as that of TABLET_SET3; (v) an average load (by mole) of tablets of TABLET_SET1 is $LM_1$; (v) an average load (by weight) of tablets of TABLET_SET3 is $LM_3$; (vi) and a ratio between $LM_1$ and $LM_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 10.

In some embodiments, the plurality of containers comprises a third container, such that (i) at least a majority of tablets within the first container are members of TABLET_SET1 (ii) at least a majority of tablets within the third container are members of TABLET_SET3; (iii) all tablets of TABLET_SET1 are of the first type and comprise the same precursor PREC_1; (iv) all tablets of TABLET_SET3 are of the first type and comprise the same precursor PREC_1 that is the same as that of TABLET_SET3; (v) an average volume of tablets of TABLET_SET1 is $VOL_1$; (v) an average volume of tablets of TABLET_SET3 is $VOl_3$; (vi) and a ratio between $VOL_1$ and $VOL_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 10.

In some embodiments, all tablets of TABLET_SET1 have substantially the same volume and/or substantially the same load (by weight) of precursor PREC_1 and/or substantially the same load (by mole) of precursor PREC_1.

In some embodiments, all tablets of TABLET_SET3 have substantially the same volume and/or substantially the same load (by weight) of precursor PREC_1 and/or substantially the same load (by mole) of precursor PREC_1

A system for preparing a hair-coloring composition comprising: a. a plurality of containers including first and second containers; b. a plurality of tablets disposed within each of the containers, each tablet comprising at least one of (i) permanent hair-coloring dye precursor and (ii) permanent hair-coloring dye coupler such that, a majority (e.g. at least a substantial majority) of the tablets in the first container comprise permanent hair-coloring dye precursor and are substantially free of permanent hair-coloring dye coupler, a majority of the tablets in the second container comprise permanent hair-coloring dye coupler and are substantially free of permanent hair-coloring dye precursor; c. a dispenser configured to dispense the tablets so as to provide multi-container tablet combinations comprising tablets from the first and second containers.

In some embodiments, dispenser is configured to dispense the multi-container combinations in accordance with at least one of (i) a hair coloring target and/or (ii) hair spectroscopy data.

A system for dispensing cosmetic ingredients comprises: a. a dispensing device; b. a plurality of containers, each containing a different respective cosmetic agent stored therein having different respective cosmetic properties, each container encoded with respective data describing both (i) reference physical-chemical property(ies) of the cosmetic agent stored therein and (ii) an ageing metric describing an extent of aging of the cosmetic material; and c. a code-reader included in or operatively linked to the dispensing device, the code-reader being configured to read the respective encoded reference physical-chemical property(ies) and ageing metrics from each of the containers, wherein: i. the dispensing device is configured, when the containers are engaged thereto, to dispense cosmetic agents from the containers in relative quantities determined in accordance with estimations of current physical-chemical property(ies) of the cosmetic agents stored within the containers; and ii. the estimations of current physical-chemical properties of each cosmetic agent are computed in accordance with both (i) reference physical-chemical property(ies) of the cosmetic agent stored therein and (ii) an ageing metric describing an extent of aging of the cosmetic material In some embodiments, further comprising a first fluid-reservoir comprising an aqueous fluid (e.g. liquid) at a pH of at most 4 and a liquid or liquid dispenser configured to dispense a quantity of liquid or fluid from the first liquid reservoir in accordance with at least one of (i) the hair coloring target and (ii) the hair spectroscopy data.

In some embodiments, further comprising a first liquid-reservoir comprising an aqueous liquid or fluid comprising H2O2 and/or another oxidizing agent and a liquid (or fluid) dispenser configured to dispense a quantity of liquid from the first liquid reservoir in accordance with at least one of (i) the hair coloring target and (ii) the hair spectroscopy data.

In some embodiments, pH of the liquid (or fluid) of the first reservoir is at most 4.

In some embodiments, further comprising a second liquid reservoir comprising an aqueous liquid at a pH of at most 4 and having a different oxidizing power than the liquid of the first liquid reservoir, the liquid dispenser being configured to dispense relative quantities of liquids from the first and second reservoirs in accordance with at least one of (i) the hair coloring target and (ii) the hair spectroscopy data.

In some embodiments, further comprising d. first and second reservoirs respectively containing first and second aqueous solutions, each aqueous solution comprising a pH regulating agent configured to maintain a pH in a range between 1 and 4 (e.g. between 1.5 and 4 or between 2 and 4 or between 2.5 and 4 or between 3 and 4), each aqueous solution having a 25 degrees C. viscosity of at most 150 cP (e.g. at most 150 cP or at most 125 cP or at most 100 cP or at most 75 cP), the first aqueous solution containing an oxidizer and having an oxidizing strength equivalent to an aqueous solution of at least X wt. % hydrogen peroxide, and the second aqueous solution having an oxidizing strength equivalent to an aqueous solution of at most 0.1 X wt. % hydrogen peroxide, the value of X being at least 1; and e. a liquid dispenser configured to respectively dispense first and second quantities of the first and second aqueous solutions from the first and second reservoirs in accordance with at least one of (i) the hair coloring target and (ii) the hair spectroscopy data.

In some embodiments, further comprising: d. first and second reservoirs respectively containing first and second aqueous solutions, each aqueous solution comprising a pH regulating agent configured to maintain a pH in a range between 1 and 4 (e.g. between 1.5 and 4 or between 2 and 4 or between 2.5 and 4 or between 3 and 4), each aqueous solution having a 20 degrees C. viscosity of at most 150 cP (e.g. at most 150 cP or at most 125 cP or at most 100 cP or at most 75 cP), the first aqueous solution containing an oxidizer and comprising at least X wt. % hydrogen peroxide, and the second aqueous solution being free of hydrogen peroxide or comprising at most 0.1 X wt. % hydrogen peroxide, the value of X being at least 1; and e. a liquid dispenser configured to respectively dispense first and second quantities of the first and second aqueous solutions from the first and second reservoirs in accordance with at least one of (i) the hair coloring target and (ii) the hair spectroscopy data.

In some embodiments, a value of X is at least 1.5 or at least 2 or at least 2.5 or at least 3 or at least 4 or at least 5.

In some embodiments, the aqueous solution of the first reservoir has an oxidizing strength equivalent to an aqueous solution of at most 24 wt. %, at most 20 wt. %, at most 16 wt. %, at most 12% wt., at most 8 wt. %, at most 7 wt. %, at most 6 wt. %, at most 5 wt. %, at most 4 wt. %, at most 3 wt. %, at most 2 wt. % or at most 1 wt. % hydrogen peroxide.

In some embodiments, the first aqueous solution comprises at most 24% wt. hydrogen peroxide.

BRIEF DESCRIPTION OF THE DRAWINGS

FIGS. 5-13 relate to methods and apparatus for optically acquiring data (e.g. spectral data) from keratinous fiber(s).

DETAILED DESCRIPTION OF EMBODIMENTS

Figure 1:
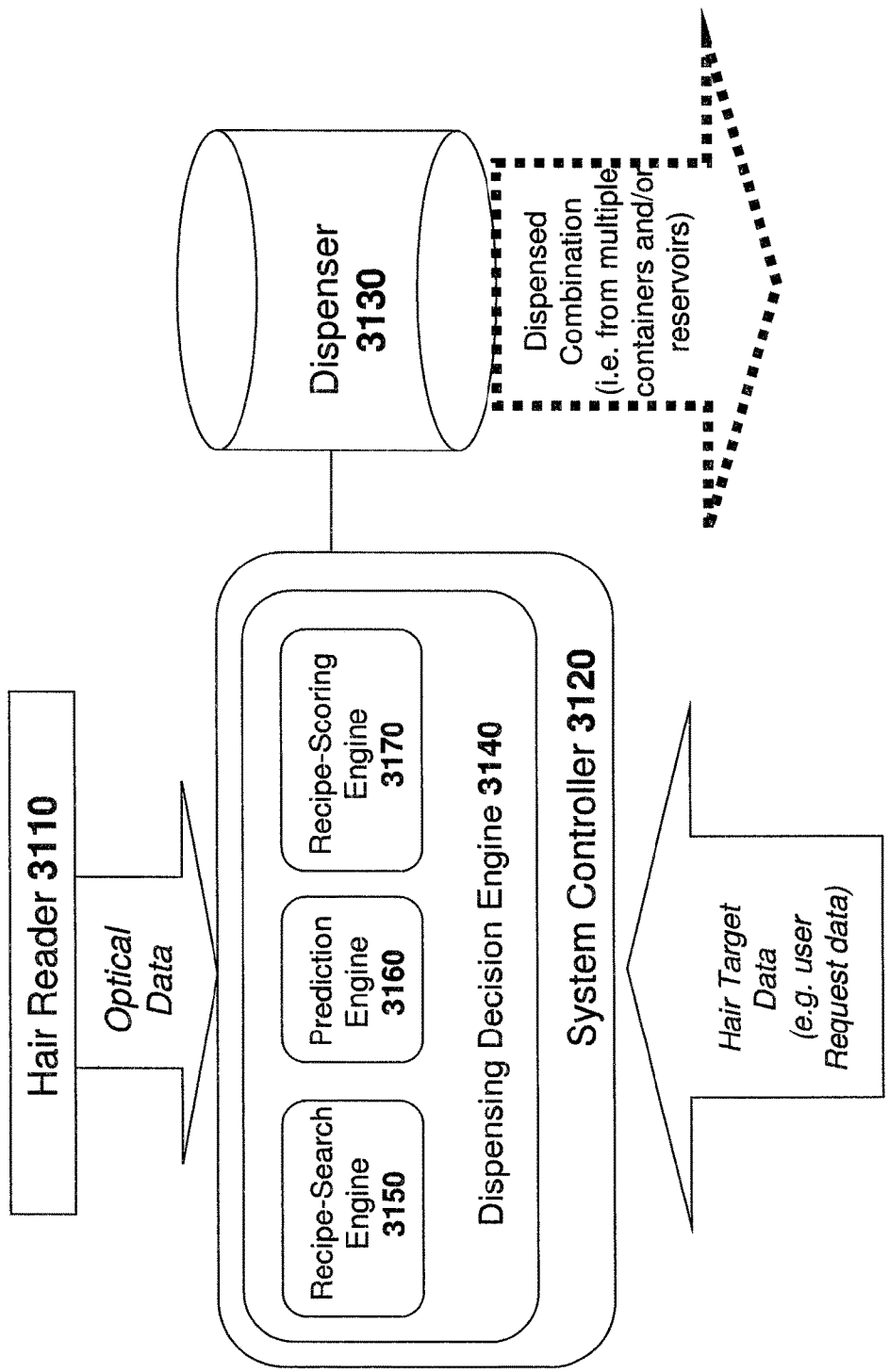
FIG. 1 is a block diagram of a system for preparing a customized hair-coloring composition in accordance with measured optical properties of the user's hair.

The claims below will be better understood by referring to the present detailed description of example embodiments with reference to the figures. The description, embodiments and figures are not to be taken as limiting the scope of the claims. It should be understood that not every feature of the presently disclosed methods and apparatuses is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to'), rather than the mandatory sense (i.e. meaning "must").

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

For the present disclosure, an "image" refers to one or more of (i) an image that is focused in both dimensions of an image plane (hereinafter a '2D-focused image') and (ii) an 'only-1D-focused-image' that is focused in only a first dimension of the image plane and blurred in the second dimension of the image plane that is orthogonal to the first dimension. In the context of images, 1D refers to a single dimension (one-dimension) within the image plane and 2D refers to two dimensions within the image plane. The only-1D-focused-image image may be generated using any optics known in the art including but not limited to a toric lens—the skilled artisan will appreciate that other lenses or other optical components other than lenses (e.g. mirrors) may be used. The terms 'partial image' and a 'only-1D-focused-image' are used interchangeably.

An 'at least 1D-focused image' refers to either an 'only-1D-focused-image' or to a '2D-focused image.' Thus any reference to 'an at least 1D-focused image' means that (i) in some embodiments, the image may be an "only-1D-focused-image" and (ii) in other embodiments, the image may be a '2D-focused image.'

Any reference to an 'image' without specifying the number of dimensions in which the image is focused may relate either to an 'only-1D-focused-image' (in some embodiments) or to a '2D-focused image' (in other embodiments).

When an image is formed at an 'intermediate location' this means that either (i) a 2D-focused image is formed at the intermediate location (e.g. at a single intermediate location); (ii) only one only-1D-focused-image is formed at a single intermediate location or (iii) first and second only-1D-focused-images (i.e. respectively focused in first and second directions (for example, the first and second directions are orthogonal to each other) and respectively blurred in orthogonals to the first and second directions) are formed in first and second intermediate locations. Thus, an 'intermediate location' refers to one or more intermediate locations.

For the present disclosure, 'color-dispersion optics' refers to optical components which breaks light into spectral components. Examples of color-dispersion optics include but are not limited to a prism and a grating.

A "light detector" or a "detector" refers to one or more photodetectors—e.g. configured as an image sensor and/or in a 1D or 2D array of photodetectors. In another example, a scanning detector apparatus equivalent to a 1D or 2D 'starting' array of photodetectors is used. When light is focused in an image plane at the light detector, the photodetector of the light detector is within the image plane.

A 'slit' is a particular type of aperture having a relatively high aspect ration—i.e. a length significantly exceeds a width thereof. For the present disclosure, for any embodiment requiring or reciting a 'slit,' an aperture may be substituted.

The term "color-imparting agent" refers to a hair-coloring agent (e.g. for example, for permanent hair-coloring) or to an ingredient thereof.

Unless otherwise specified, the term "coupler" refers to "dye coupler" and the term "precursor" refers to "dye precursor." The term "hair color-imparting agent" or simply "color-imparting agent" refers to a hair-coloring agent (e.g. for example, for permanent hair-coloring) or an ingredient thereof. "Hair color-imparting agent" and "color-imparting agent" are used interchangeably. A "Permanent hair color-imparting agent" refers to one of (i) 'color-imparting agent' for permanent hair-coloring or (ii) an ingredient thereof.

Dye precursors are generally aromatic diamines, diaminophenols, and/or aminophenols with an amine or hydroxy group ortho or para to an amine group. Pyrimidine and pyrazole derivatives (e.g., substituted pyrimidine, substituted pyrazole), used to develop shades with red highlights, are also generally considered to be dye precursors.

Dye couplers are oxidation dye intermediates which, on their own, yield only feeble coloring through oxidation, but can be combined with dye precursors to produce stronger shades. The amine and/or hydroxy groups substituting dye couplers are frequently in meta position to each other. Dye couplers include m-phenylene-diamines, m-aminophenols, naphthols, resorcinols, polyphenols, pyrazolones and their derivatives.

A "substantial majority" means at least 75%. In some embodiments, a 'substantial majority' is at least 90% or at least 95% or at least 99%. Unless specified otherwise, a 'majority' means 'at least a majority.' Unless specified otherwise, 'at least a majority' means that, in some embodiments, the 'majority' is at least a substantial majority—i.e. at least 75% or at least 90% or at least 95% or at least 99%.

The terms "color imparting agents", "color imparting compounds", "color imparting ingredients" and "coloring agents" are interchangeably used herein, and encompass any compound used to impart a color by introducing a colored substance (e.g., dye, pigment), including, but not limited to, oxidation dye precursors, oxidation dye couplers, direct dyes, and any combination thereof.

In this specification, by "pH adjusting agent" is meant a compound or salt that is added to a solution to lower or raise the pH of the solution. It will be appreciated that in some instances, the pH adjusting agent may function as a buffer; in such instances, the pH adjusting agent may also be referred to as a pH regulating agent. A "dry" tablet will be understood as being a tablet containing not more than 10 wt. %, not more than 9 wt. %, not more than 8 wt. %, not more than 7 wt. %, not more than 6 wt. %, not more than 5 wt. %, not more than 4 wt. %, not more than 3 wt. %, not more than 2 wt. %, or not more than 1 wt. % water.

The term 'load of a tablet' comprising color-imparting agent relates to the weight or moles of the active hair-coloring ingredient.

Unless otherwise specified, a "viscosity" of a substance is as measured at a shear rate of $10\ s^{-1}$ and at a temperature of 25° C. Unless otherwise specified a "25° C. viscosity" is measured at a shear rate of $10\ s^{-1}$.

The "abbreviation" cP refers to centipoise (cP). Unless otherwise specified, 'viscosity' refers to the 'dynamic viscosity.'

The term 'fluid' refers to a liquid or cream—at any viscosity e.g. of at most 150 cP or at most 125 cP or at most 100 cP or at most 75 cP The term "liquid dispenser" is used broadly to relate to a dispenser of any flowable medium including but not limited to liquids or an emulsion or an gel or a cream. In the present disclosure 'electronic circuitry' is intended broadly to describe any combination of hardware, software and/or firmware.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

Embodiments of the invention relate to the dispensing of a "multi-container tablet combination" from a plurality of tablets. This means that for a plurality of N containers Container$_1$ . . . Container$_N$ (where N is a positive integer equal to at least 2), for two positive integers i and j (i≠j, both i and j are equal to at least 1 and at most N), at least one tablet (in some embodiments, a plurality of tablets) is dispensed from Container$_i$ and at least one tablet (in some embodiments, a plurality of tablets) is dispensed from Container$_j$.

In some embodiments, when a tablet dispenser dispenses tablets a tablet "in accordance with one or more properties" (e.g. a hair coloring target and/or hair spectroscopy data), the quantity of tablets (i.e. number and/or volume and/or weight—for example, relative quantities of tablets from multiple containers where different types of tablets are stored in each container) is determined according to the properties—for example, by electronic circuitry—for example, according to some algorithm predicting an outcome of a hair coloring.

In some embodiments, a liquid dispenser may dispense a flowable medium (e.g. a liquid or cream or gel or emulsion) "in accordance with one or more properties" (e.g. a hair coloring target and/or hair spectroscopy data)—this may refer to the quantity of flowable medium—for example, absolute quantities or relative quantities of flowable medium relative to tablets or relative quantities of one flowable medium (i.e. in a first reservoir) relative to another flowable medium (i.e. in a second reservoir). This may, for example, be carried out to dilute a flowable medium of one of the reservoirs with that or another reservoir. The determining may be carried out for example, by electronic circuitry—for example, according to some algorithm predicting an outcome of a hair coloring.

Solid formulations, suitable for use in the treatment of keratinous fibers are disclosed herein. According to some embodiments of the present invention, the solid formulations have a form of tablets comprising a superdisintegrating agent, which imparts advantageous features to the tablet. The solid formulations disclosed herein may further comprise color imparting agents (such as dye precursors, dye couplers and direct dyes), and can be used in combination with, or can further comprise, other agents for treating keratinous fibers, such as alkalizing agents and oxidizing agents.

Figure 2:
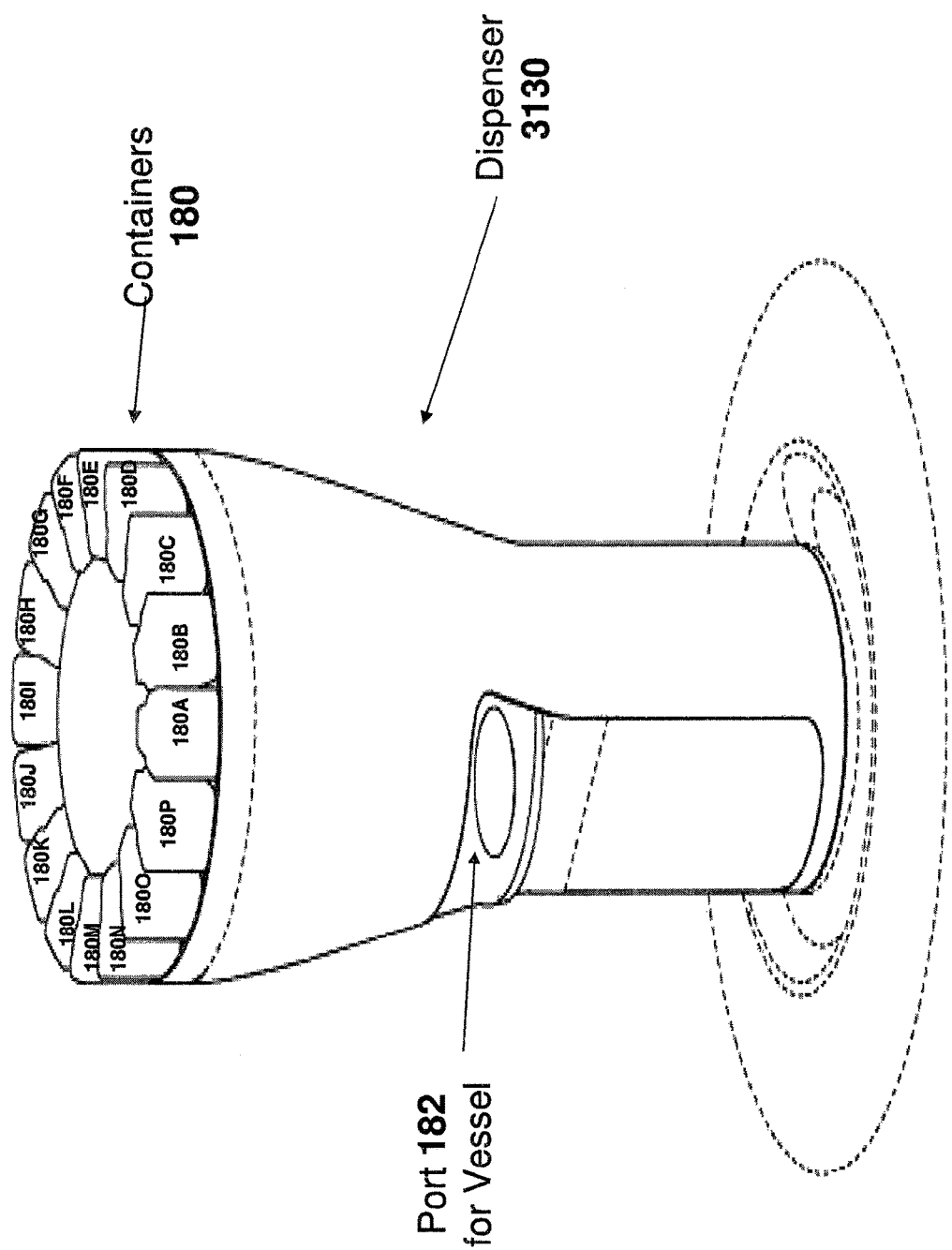
FIGS. 2 and 3 respectively illustrate example dispenser and hair-reader devices.

FIG. 1 is a block diagram of a system for preparing a customized hair-coloring composition in accordance with measured optical properties of the user's hair. FIGS. 2 and 3 respectively illustrate example dispenser and hair-reader devices—e.g. useful in the system of FIG. 1. FIG. 4 is a flow-chart of a routine for preparing a hair-coloring composition—for example, using the system of FIG. 1.

FIGS. 5-13 relate to methods and apparatus for optically acquiring data (e.g. spectral data) from keratinous fiber(s). For example, a plurality of spectra of the keratinous fiber(s) may be detected such that each spectrum corresponds to (i) a different respective portion of the keratinous fiber(s) and/or (ii) material within a different sub-region of space within which at least a portion of the keratinous fiber(s) are disposed.

Figure 14A:
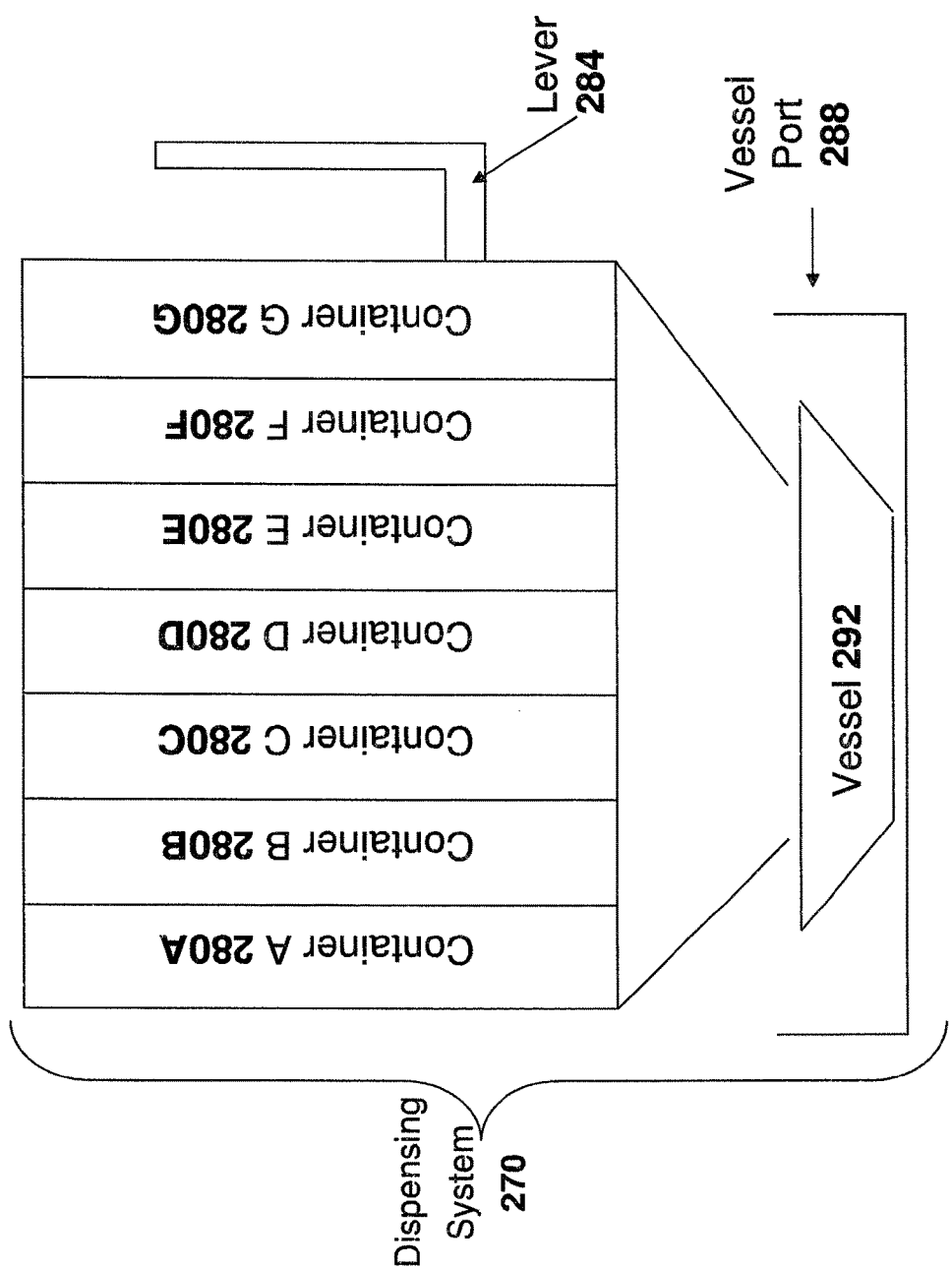
FIGS. 14-15 relate to a dispenser system for preparing compositions for oxidative hair-coloring.
Figure 14B:
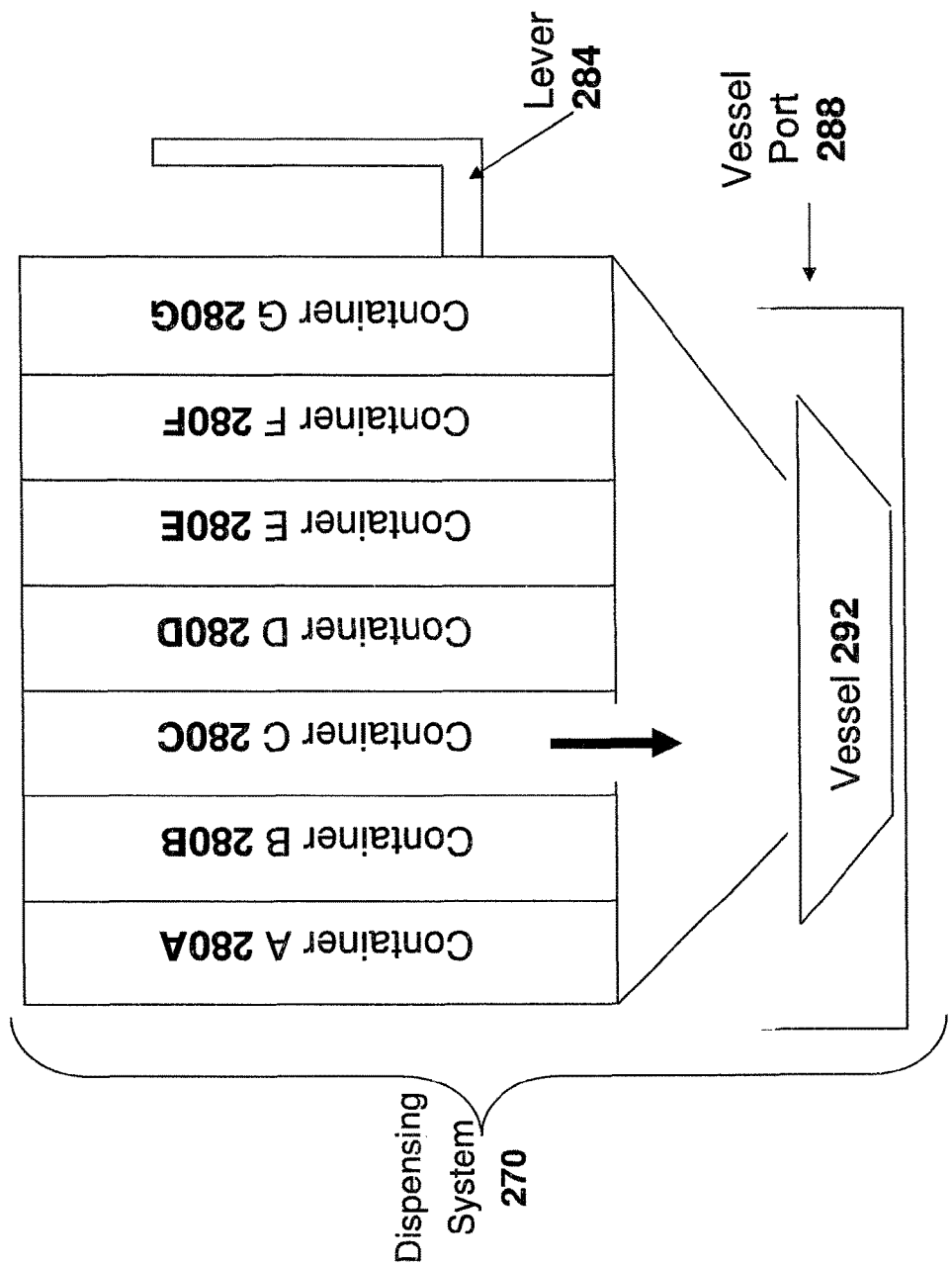
Figure 14C:
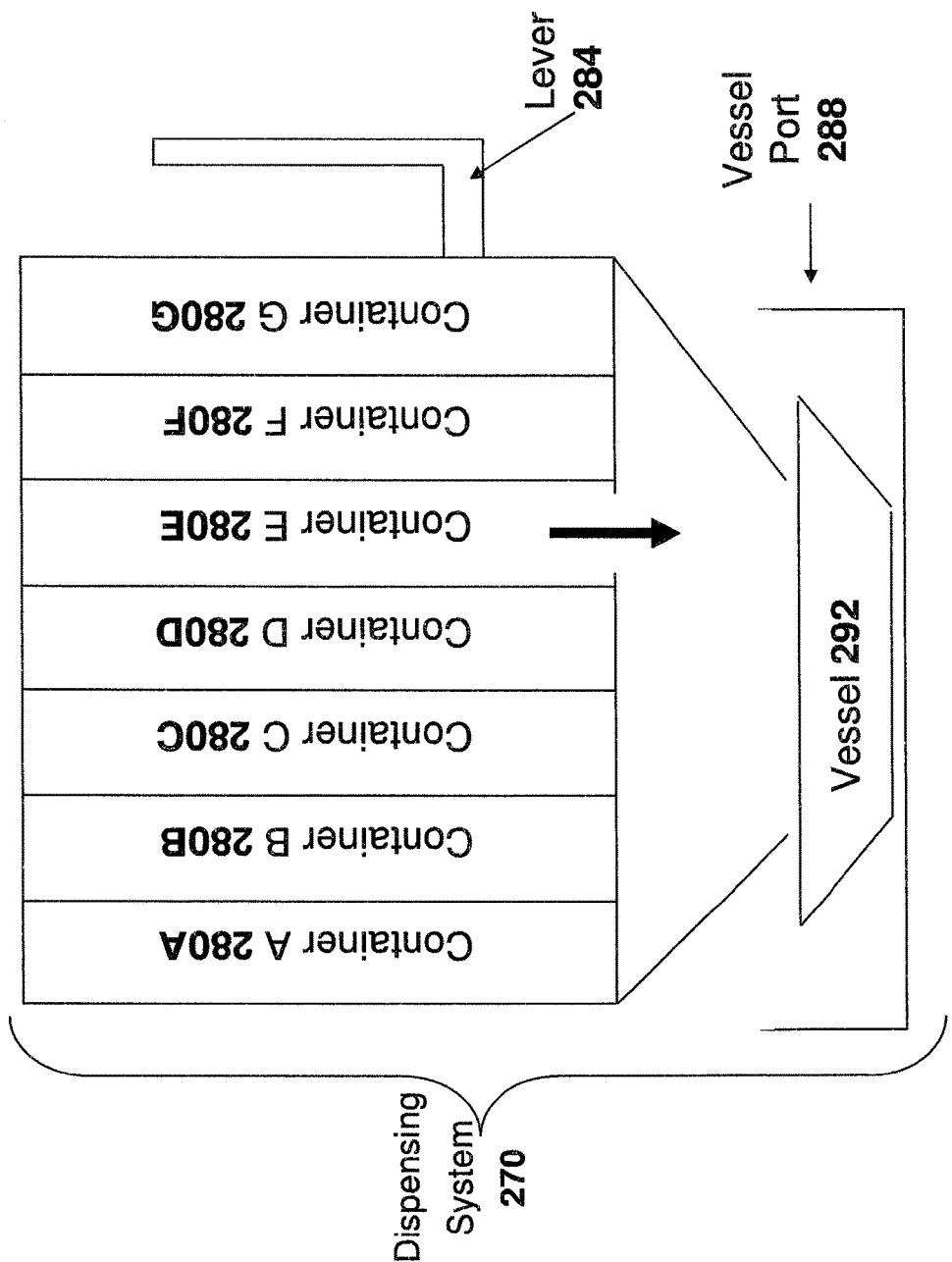
Figure 15:
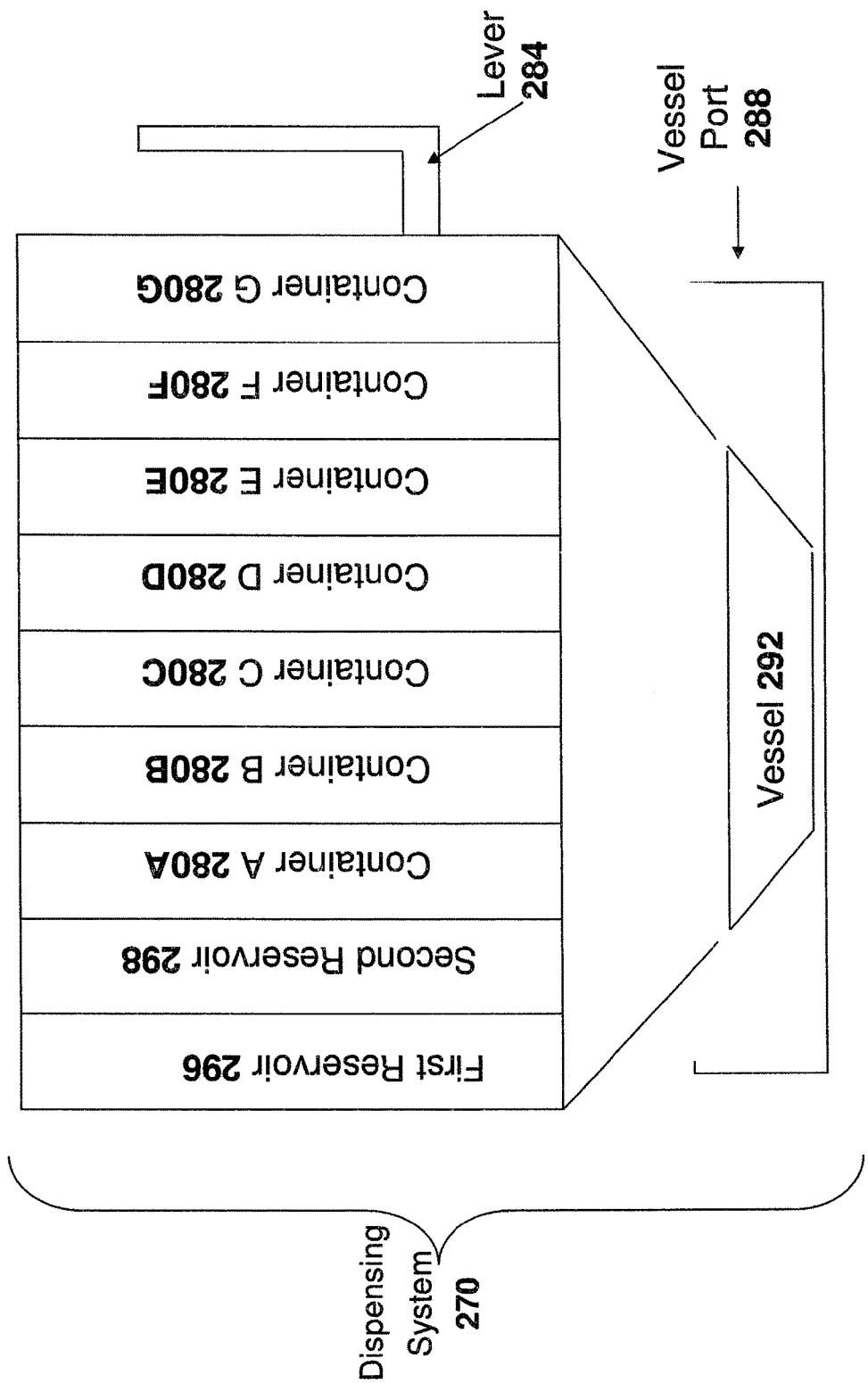
Figure 16:
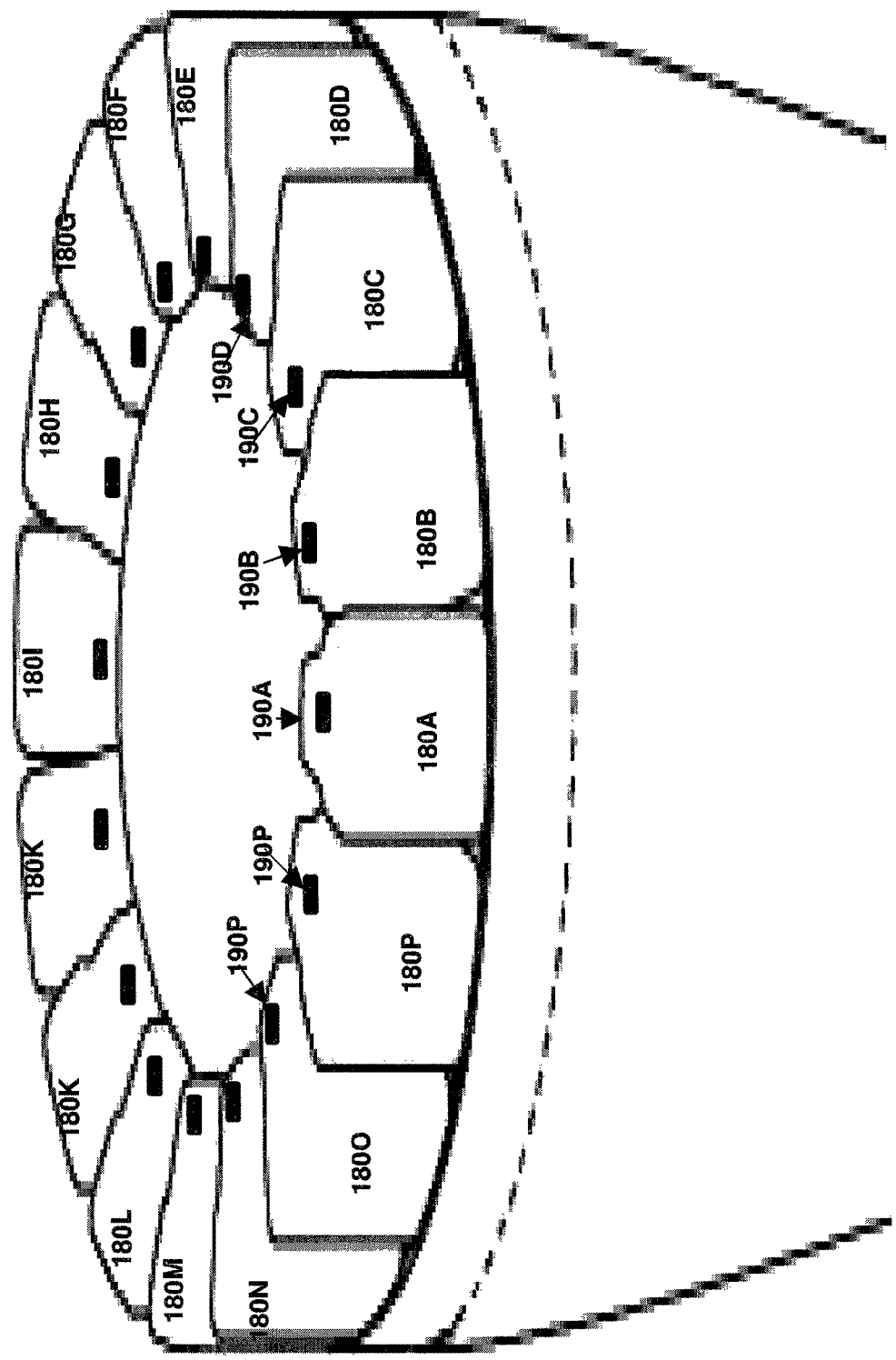
FIGS. 16-19 relate to dispensing of cosmetic agents according to data read from a container in which the cosmetics agents are stored.
Figure 17:
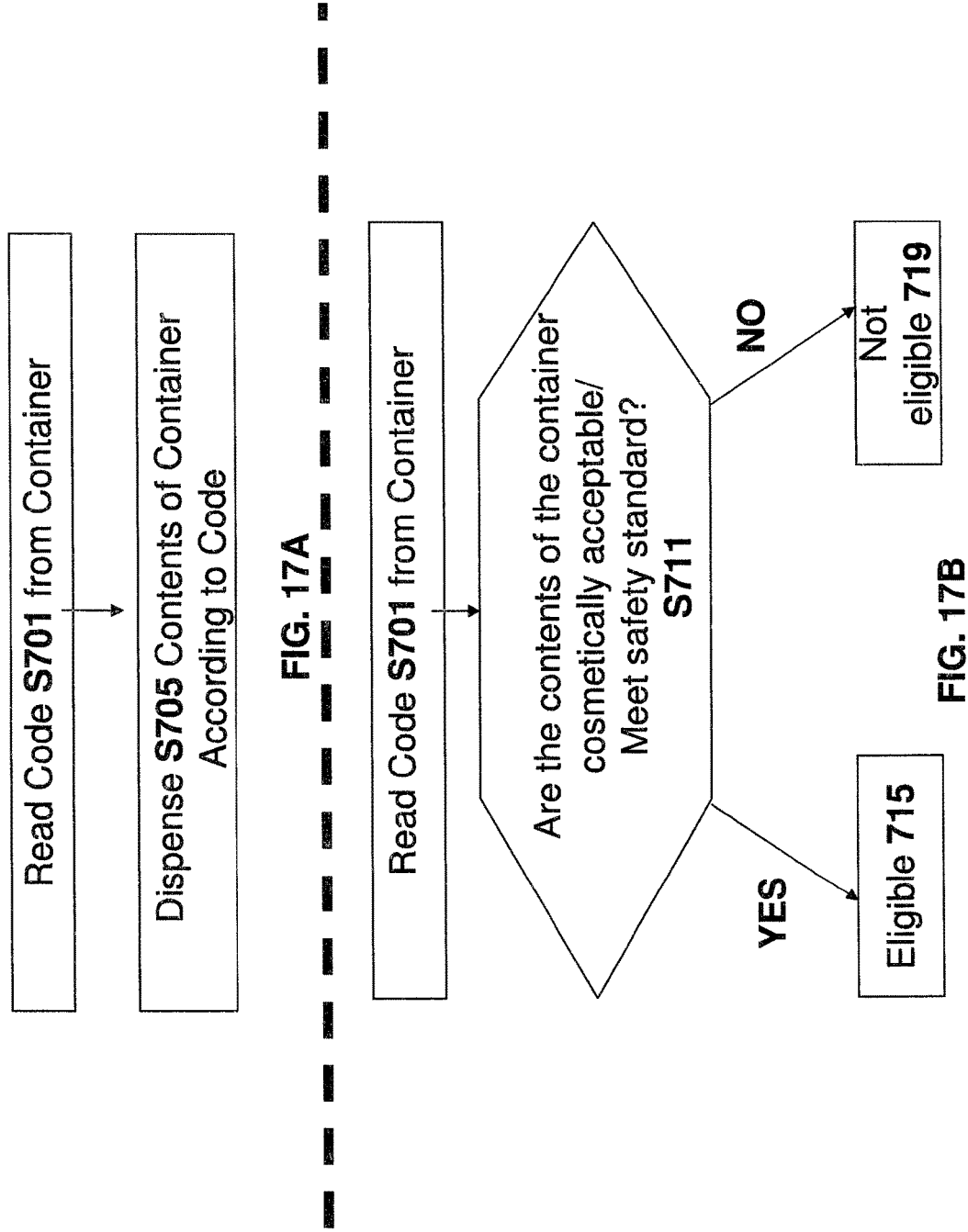

FIGS. 14-15 relate to a dispenser system for preparing compositions for oxidative hair-coloring. In particular, it is possible to segregate dye precursor from couple such that some of the containers of the dispenser system contain dye precursor and are substantially free of coupler while other containers contain coupler and are substantially free of dye precursor. A dispenser device is configured to dispense contents of the containers to provide multi-container combinations comprising material from the first and second containers.

FIGS. 16-19 relate to dispensing of cosmetic agents (e.g. for hair-coloring or for any other cosmetic application) where for each container, data describing physical and/or chemical properties of the cosmetic material therein is encoded on the container. This data is read by a code-reader operatively linked to a dispensing device which dispenses the cosmetic material from the containers according to the data reader from the containers.

A Discussion of FIGS. 1-4

FIG. 1 is a block diagram of a system for (i) measuring optical properties of hair and, (ii) in accordance with the measured optical properties, dispensing material from containers to provide a customized hair-coloring composition. For example, a user desires to color his/her hair to a target shade. An optical measurement of the user's "initial hair" is performed, and a hair-coloring composition, customized according to the initial state of the user's hair as well as the hair-coloring target is prepared.

Illustrated in FIG. 1 are hair reader 3110, system controller 3120, and dispenser device 3130. In the non-limiting example of FIG. 1, system controller 3120 includes dispensing decision engine 3140 which includes recipe-search engine 3150, prediction engine 3160 and recipe-scoring engine 3170.

Hair reader 3110 acquires optical data from hair—for example by illuminating the hair and detecting light reflected by and/or transmitted by and/or deflected by the hair. System controller 3120 (e.g. comprising a digital computer) receives both the optical data and hair target data (e.g. describing a target shade desired the user). In accordance with the received data, the system controller 3120 computes (e.g. dispensing decision engine 3140) using a customized recipe for the hair-coloring composition—e.g. including respective quantities of a plurality of different materials stored in dispenser 3110.

The dispenser proceeds to dispense the materials (e.g. into a mixing vessel—NOT SHOWN in FIG. 1) for the hair-coloring composition. These materials may be automatically or manually mixed to form a customized hair-coloring composition, which is applied to the user's hair.

One non-limiting example of a dispenser 3130 of hair-coloring agents is illustrated in FIG. 2. In this non-limiting example, a plurality of containers 180A-180Q are engaged to dispenser 3130, such that each container contains therein different respective material related to hair-coloring. Dispenser 3130 dispenses a combination of these material into a mixing vessel (NOT SHOWN)—e.g. located in port 182.

In the example of FIG. 1, system controller 3120 includes dispensing decision engine 3140 which computes (a) preferred recipe(s) for dispensing material for the hair-coloring composition. Towards this end, a number of candidate recipes may be considered, selected from a relatively 'large' number of possibilities by receipt-search engine 3150 (For each candidate recipe, the predicted outcome of treating the user's hair according to the candidate recipe may be computed by prediction engine 3160 and scored by scoring engine 3170. For example, scoring engine 3170 may compare the predicted outcome with the hair-target data describing the shade desired by the user.

In one example, one or more of 3140, 3150, 3160, and/or 3170 is implemented as software stored in volatile or non-volatile memory).

Figure 3A:
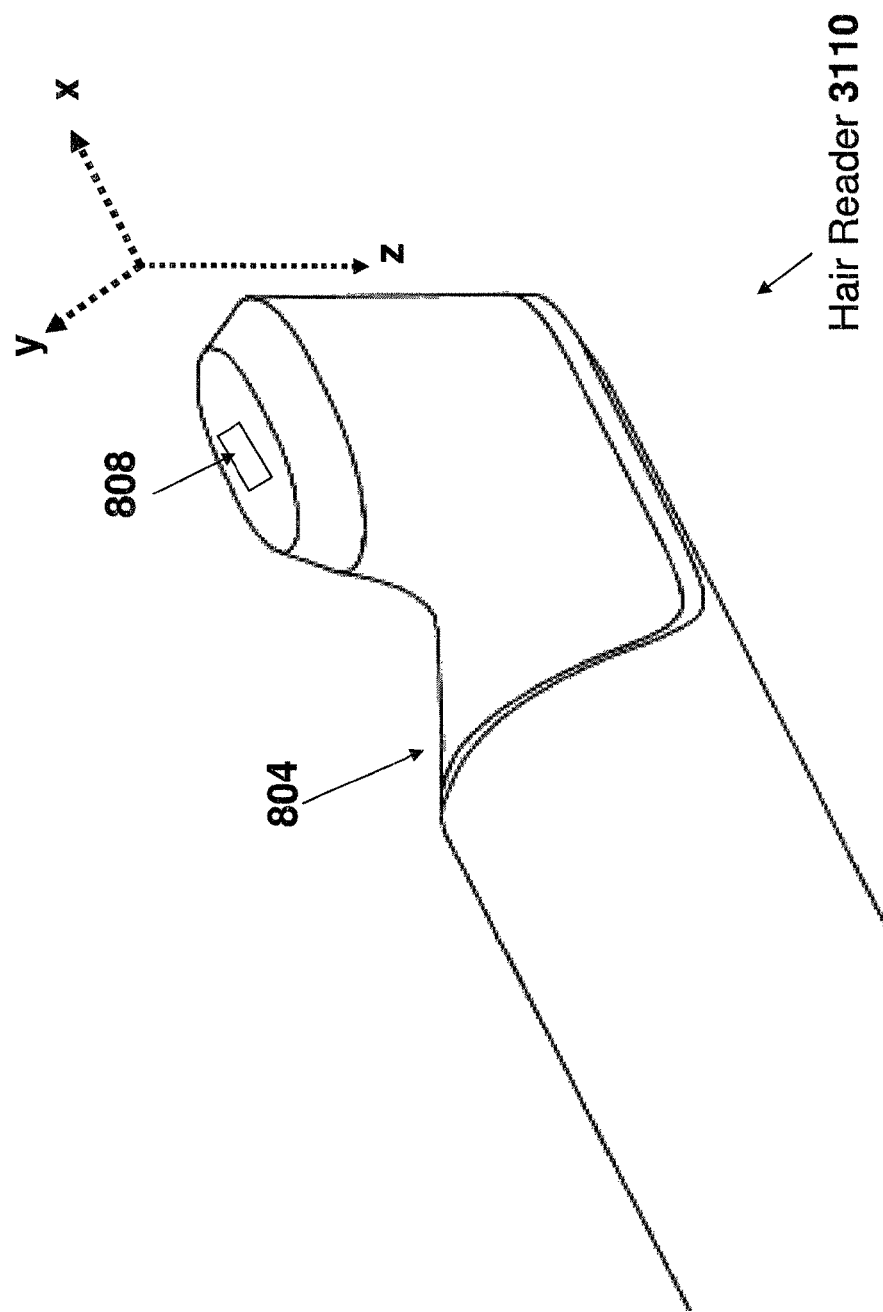
Figure 3B:
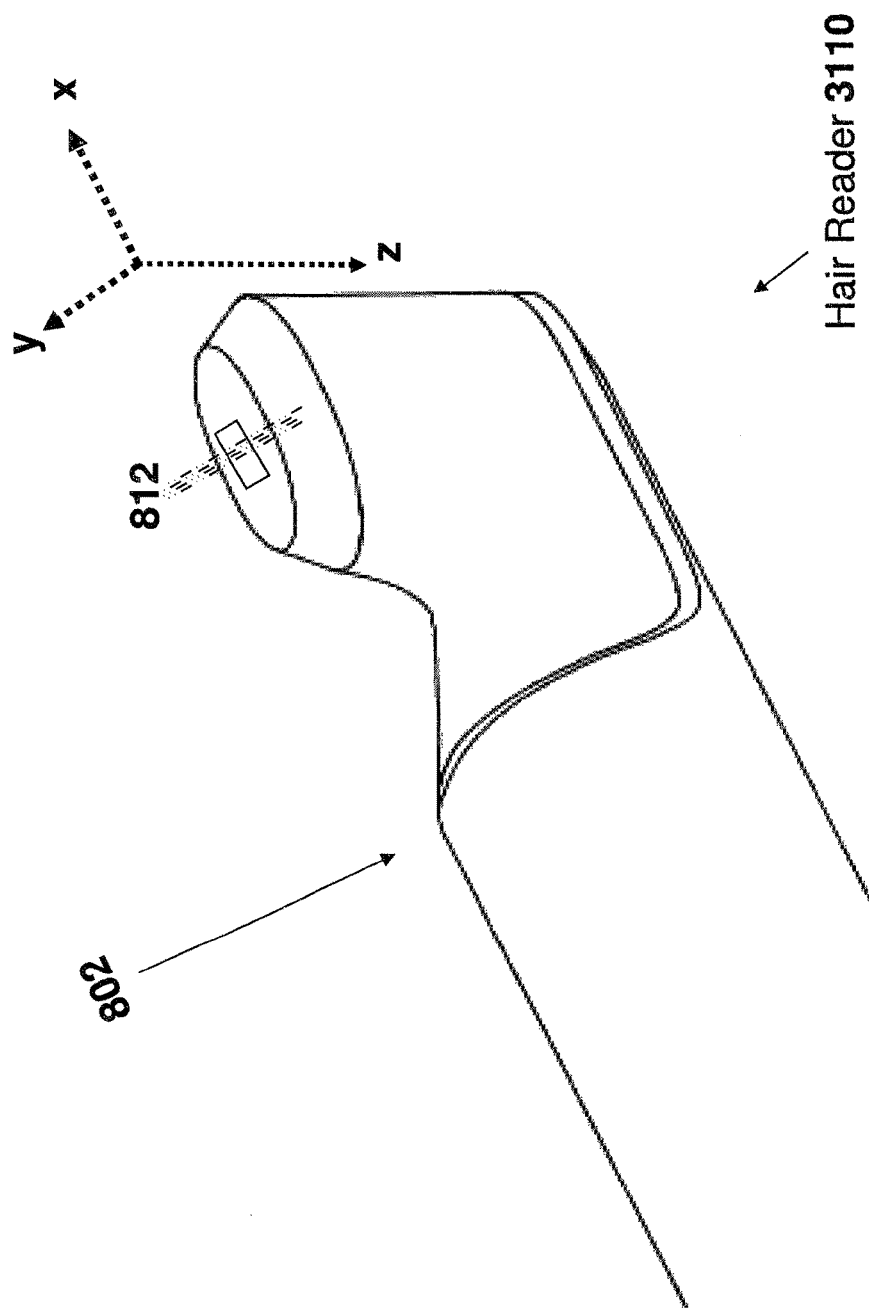
Figure 4:
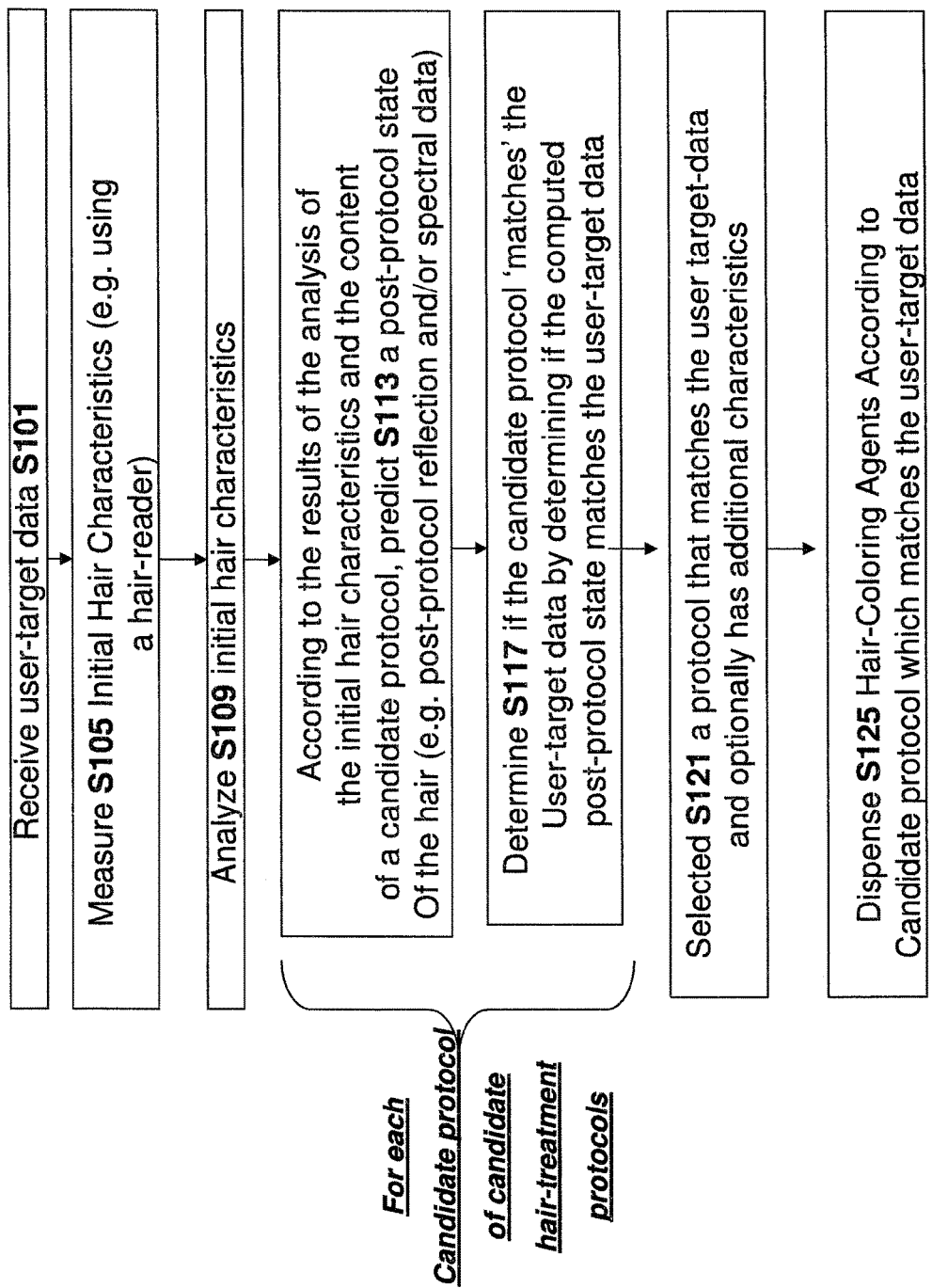
FIG. 4 is a flow-chart of a routine for preparing a hair-coloring composition.

FIGS. 3A-3B illustrate a non-limiting example of a hair-reader 3110 in accordance with some embodiments. Hair-reader 3110 includes a housing 804 (e.g. opaque) and a window 808. In FIG. 3B, a plurality of keratinous fibers 812 are substantially aligned along an alignment axis which corresponds to the 'y' axis.

FIG. 4 is a flow-chart of a non-limiting example of a technique for hair-coloring for example, using the system of FIG. 1. In step S101, user-target data is received and stored (e.g. in volatile and/or non-volatile computer-readable storage). Typically, the user-target data relates to a selected shade or color—e.g. a user desires to color his/her hair to the selected shade or color. In step S105, characteristic of a user's hair are measured—e.g. using at least a hair-reader device (e.g. for measuring at least one hair-reflection value or for measuring a hair-reflection-spectrum(a)) such as that illustrated in FIG. 2 or 4 or that disclosed in PCT/IB2012/051351 or any related hair-reader device, as discussed below. These characteristics may be electronically analyzed in step S109. According to the technique of FIG. 4, it is possible to compute a 'customized' hair-treatment that is specific to (i) an initial pre-treatment state of the user's hair (e.g. as measured in step S105 and analyzed in step S109) and (ii) the user-target data.

The term 'user-target' typically includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' may refer to any one of: (A) content of a hair-coloring composition (or more than one hair-coloring composition which may be applied sequentially or simultaneously—for example, a dye-containing composition and a bleaching composition) to be applied to the hair and/or (B) other treatment parameters—e.g. treatment durations, treatment temperature. Computing or specifying a 'hair-treatment' may include specifying at least absolute or relative quantities or 'loads' (i.e. expressed in molar terms, or as weights, or a volumes, or in any other manner known in the art) of one or more hair-coloring agents of a hair-coloring composition (e.g. a 'multi-agent' composition). The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

For the present disclosure, the term 'hypothetical' and 'candidate' are used interchangeably and refer to possible treatments that may or may not be actualized.

Typically, the specific characteristics of each user's hair is quite individual (e.g. based upon his/her genotype, age, environmental effects etc.) and the number of potential target shades or colors may also be relatively large. Because of the myriad possible combinations of initial and target hair characteristics, the number of possible candidate/hypothetical hair-treatment protocols may be extremely large, and it is not always known a priori which hair-treatment protocols are predicted to be effective (or most effective) to transform hair from its initial state to a state matching the target data received in step S101.

As such, it may be necessary to electronically analyze multiple hypothetical hair treatments to identify a treatment (or set of more than one hypothetical hair-treatments) which successfully transforms the initial hair to a target color.

This is done in steps S113 and S117. Thus, in step S113, a post-protocol state for the hair is predicted for the hair-characteristics measured in step S105 and a specific candidate hair-treatment. In step S117, it is electronically determined if this post-protocol state matches the specifications of the user target-data.

The term 'hair-color treatment' is not restricted to introducing colorants (e.g. artificial colorants) into the hair (i.e. 'coloring') but may also include hair-bleaching.

In one non-limiting example, (i) in step S105 one or more initial reflection spectrum(a) are measured, (ii) in step S113 a hypothetical post-treatment reflection spectrum is computed from the initial reflection spectrum and specifics of a candidate hair-treatment protocol, and a color value (e.g. an LAB value) is computed from the hypothetical post-treatment reflection spectrum; and (iii) in step S117 this initial-hair-specific and candidate-protocol-specific LAB value is compared to an LAB value associated with the user-target data received in step S101.

In different embodiments, it is possible to measure a reflection spectrum, a transmission spectrum, a spectrum of deflected light, and an absorption spectrum.

In step S121, a protocol that matches the user target-data is selected. Optionally, for example, if more than one candidate protocol matches the user target-data, these candidate protocols may be analyzed and/or scored, and a more preferred matching hair-coloring protocol may be selected accordingly.

In step S125, according to the selected hair-coloring protocol, respective quantities of hair-coloring agent, for a plurality of hair-coloring agents, are each dispensed according to a specifics of the hair-coloring protocol selected in step S121.

One non-limiting example of a dispenser of hair-coloring agents is illustrated in FIG. 2. In this non-limiting example, different respective hair-coloring agents are disposed in each container of a plurality of containers 180A-180Q. In response to the results of step S121, for at least 2 or at least 3 or at least 4 or at least 5 or at least any number of hair-coloring agents, respective quantities of each hair-coloring agent are dispensed into a vessel (not shown) located in port 192.

In some embodiments, the dispenser is automatic and includes electronic circuitry for regulating quantities of hair-coloring agents that are dispensed.

For the present disclosure, a dispensing a plurality of hair-coloring agents according to the results of some sort of computational and/or electronic operation(s) (e.g. a predicting of a post-hypothetical-hypothetical-hair-treatment spectrum (e.g. reflection spectrum) or a color value derived therefrom) refers to one or more of two situations: (i) a situation whereby electronic circuitry automatically controls a dispensing device (the skilled-artisan is directed to PCT/IB2012/051351 incorporated herein by reference) and/or (ii) a situation whereby hair-coloring instructions computed from an electronic predicting is communicated to a human user (e.g. visually via a computer screen or in any other manner). The hair-coloring instructions may relate to relative quantities of hair-coloring agents and the human user follows the instruction to, for example, dispense hair-coloring agent(s) according to the quantities specified by the computer-provided instructions. The container for a chemical agent may have any form factor (e.g. rigid container, tube, etc) and may either may mounted to a dispenser device as illustrated in FIG. 2 or may be a 'free' or unmounted container.

Once these agents are dispensed into the vessel, one or more steps may, optionally, be performed to transform the contents of the vessel (not shown) into a hair-coloring mixture, which may then be applied to the user's hair to color the hair.

For the present disclosures, the terms 'input keratinous fiber(s)' and 'initial hair' are used interchangeably—both refers to keratinous fibers(s) (e.g. hair) which is subjected to one or measurements (e.g. optical measurements and/or reflection measurements—for example, to measure a hair-reflection spectrum(a)) for the purpose of predicting a final state of one or more hypothetical hair-treatments.

The skilled artisan will appreciate that not every step of FIG. 4 is required in every embodiment, the order of steps of FIG. 4 is not limiting—the steps may be performed a different order, additional steps may be performed, and one or more steps may be modified.

A Discussion of FIGS. 5-13

Embodiments of the invention relate to an apparatus and method for acquiring spectral data of a group of keratinous-fibers—e.g. human hair—for example (but not limited to) in the context of steps S105 and S109. One application of the currently-disclosed system and method relates to hair-coloring—for example, computing or selecting a hypothetical hair treatment. In this example, a preferred hair treatment (e.g. computed in steps S113-S121) may depend on both (i) an initial state of the hair; and (ii) a user-specified target—e.g. a desired shade or color for the hair.

Towards this end, when characterizing the initial state of the hair (e.g. in step S109), it may be desirable to spectrally and/or automatically to distinguish between two types of hair which, to the layman and/or 'casual naked eye viewer' both share a similar 'grey hair' appearance.

The first hair-type may be what is termed as 'natural grey'—a mixture of natural-hair-pigment-containing hair shafts (e.g. melanin-containing hair shafts such as black shafts or red shafts or blond shafts or brown shafts or other naturally-colored shafts) and natural-white hair shaft (e.g. due to age, albinism, or any other reason which may naturally render hair white). The combination of the different types of hair-shaft may appear simply as 'grey' to the casual naked-eye viewer.

The second hair-type may be what is termed 'artificial grey'—hair-shafts that have been colored by artificial colorant. Typically, for the second hair-type, the hair-shafts tend to be more similar to each other with respect to color than the first hair-type. Thus, when considering, as a whole, a group of keratinous fibers (e.g. hair-shafts), it may be said that those of the second type are more homogenous with respect to color than those of the first group.

The term 'hair-type' refers to a characteristic of a multiple hair-shafts—e.g. of a 'mixture' of hair on the user's head.

Although a trained professional may be able to distinguish between the first and second hair-type, in many situations no such professional is available and/or this approach is not practical. In one non-limiting example, spectral data of the hair is acquired for the purpose of computing a predicted post-treatment hair-spectrum and an LAB value therefrom), and it may be useful to also employ spectral data to distinguish between first and second types of hair.

In different examples, various types of hair are schematically illustrated in the figures. As illustrated in FIG. 5, (i) a top or side-view of a generic hair shaft is illustrated as a 'dot-dash' pattern; (ii) a cross-section view of a generic stand is illustrated by a 'brick' pattern. FIG. 5 also relates to (i) a white-hair shaft (e.g. natural-white—e.g. substantially melanin-lacking); (ii) a black-hair shaft (e.g. natural black hair—e.g. color due to a presence of melanin); (iii) a grey hair shaft (e.g. the color is due to artificial colorants).

Figure 6:
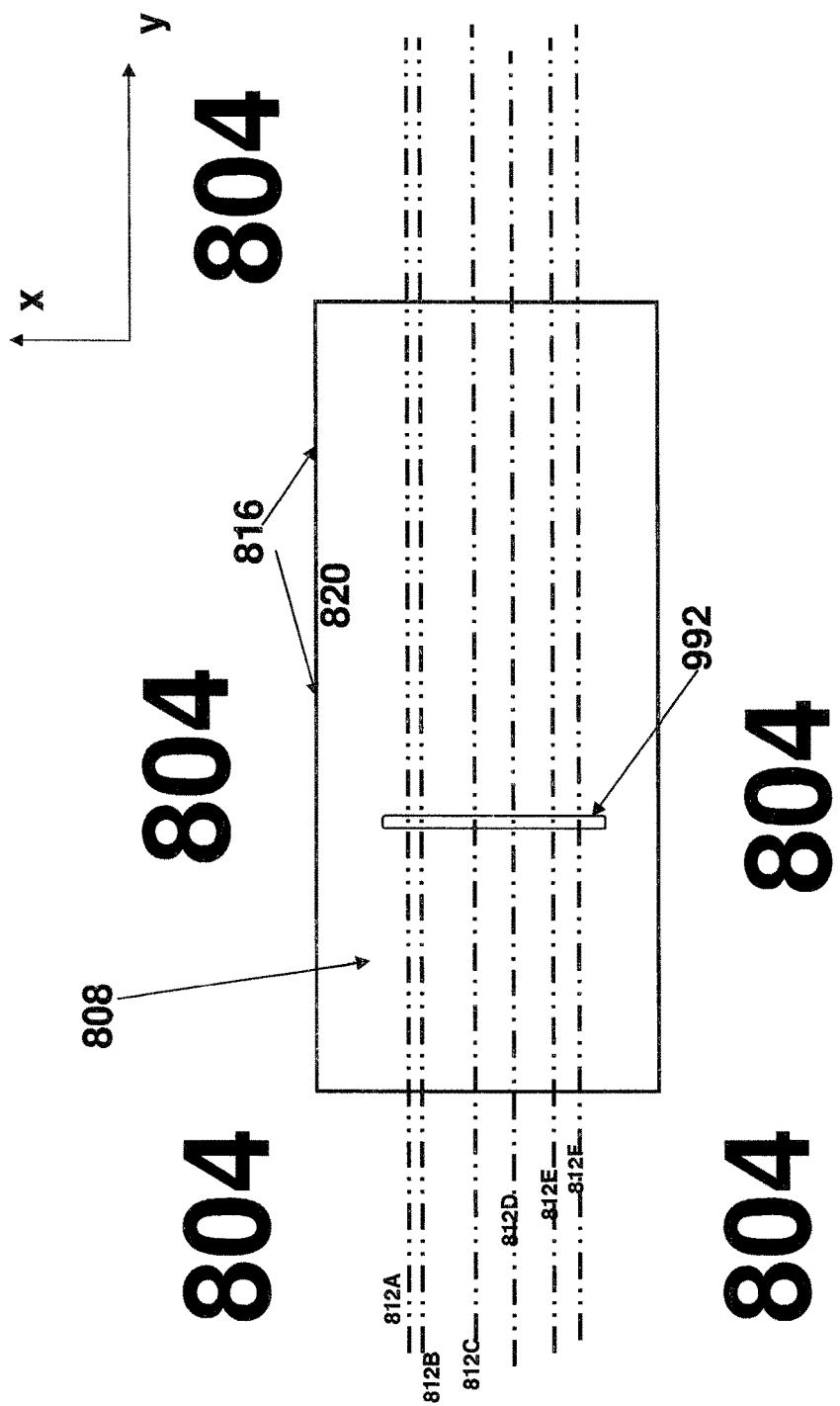

FIG. 6 is a close-up of substantially-aligned hair shafts on window 808 of hair-reading device—window 808 includes a transparent surface 820 (e.g. of glass or plastic) and a support frame 816 for supporting transparent surface 820 on housing 804.

Figure 7A:
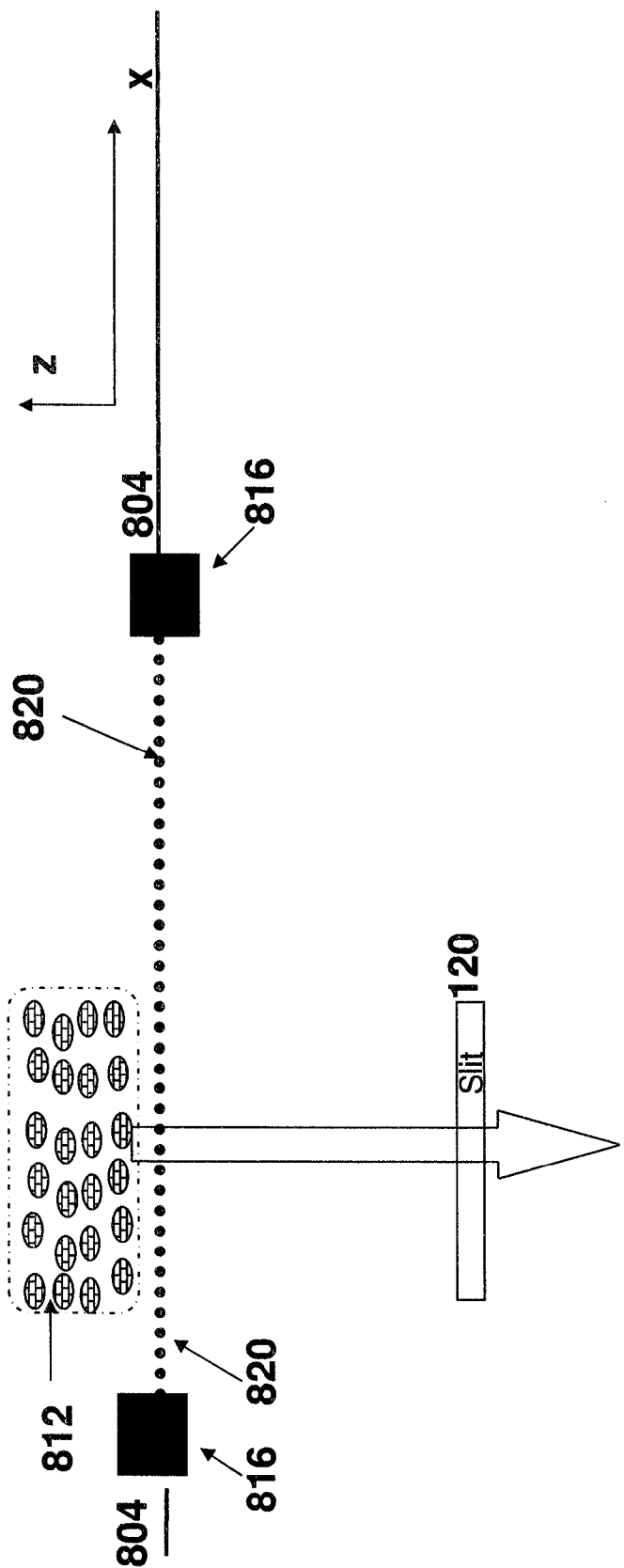
Figure 7B:
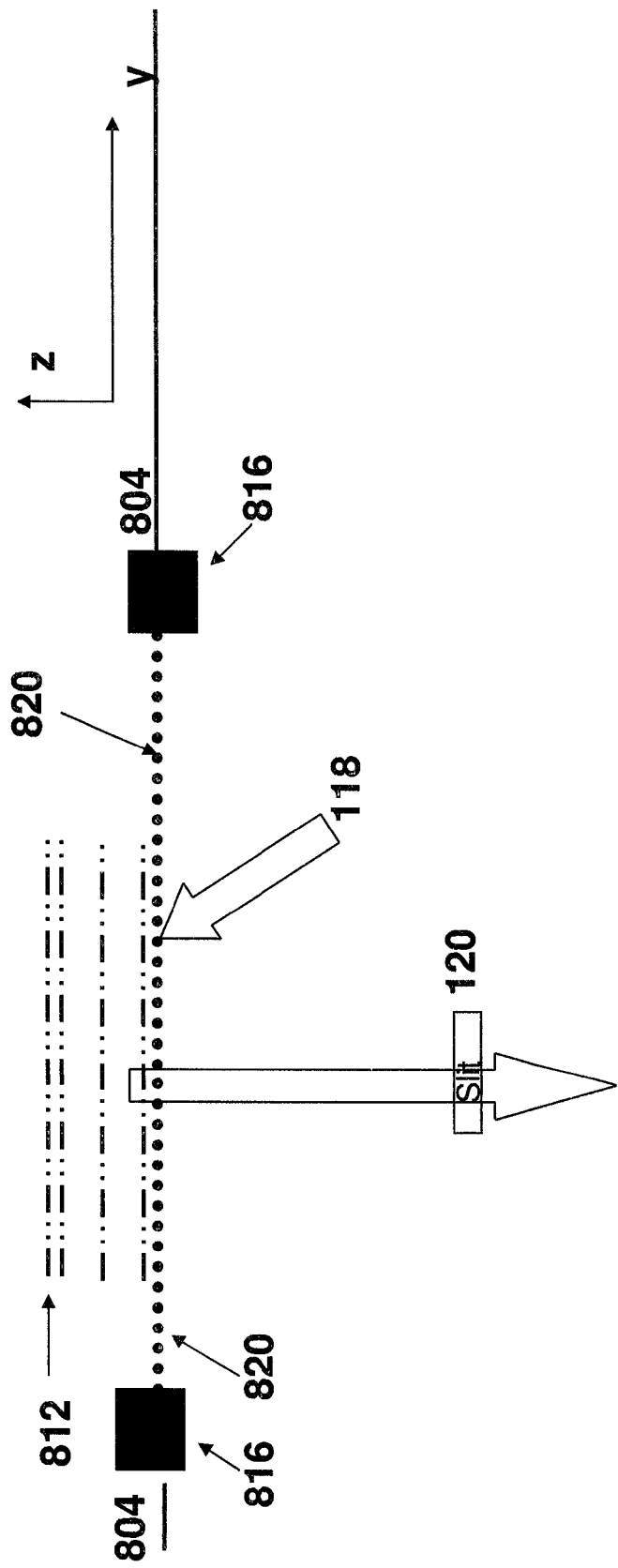
Figure 11A:
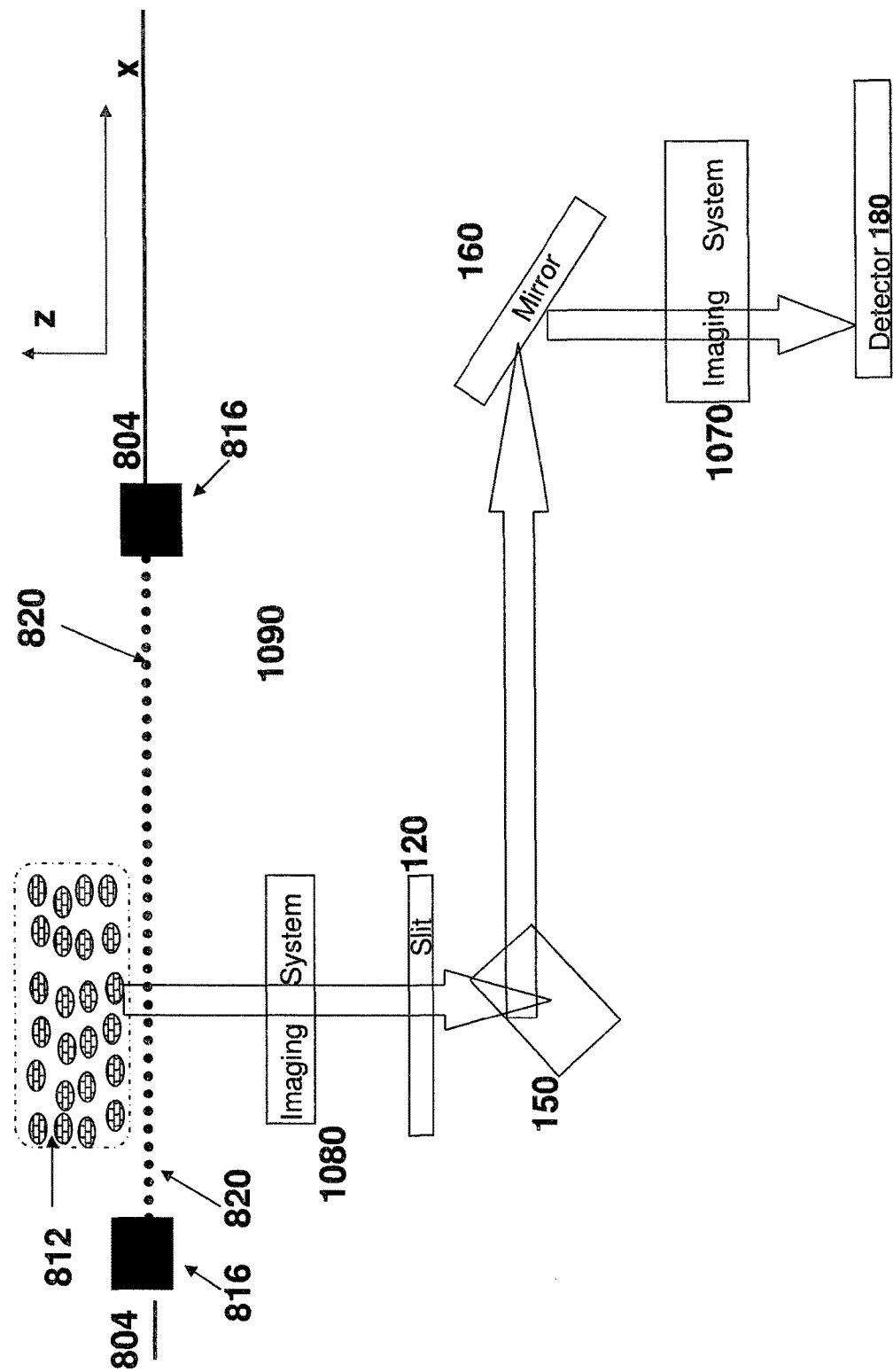
Figure 11B:
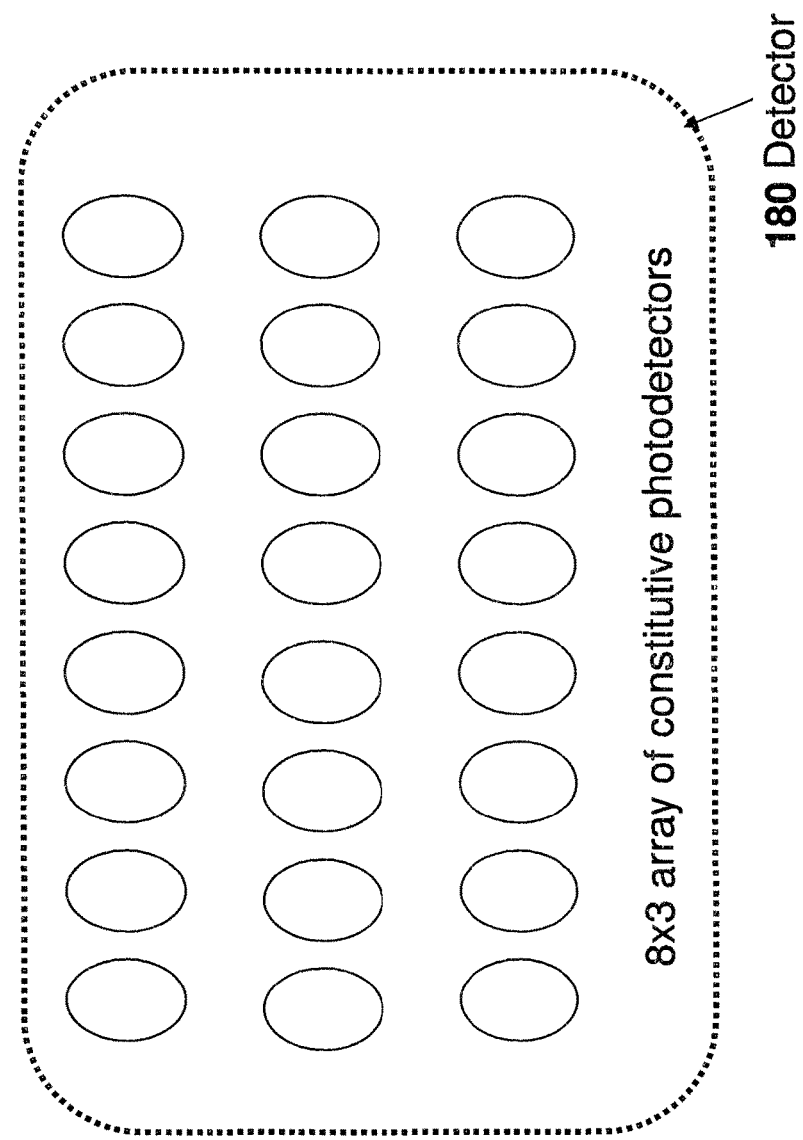

FIG. 7A-7B illustrate a plurality of keratinous fibers on a window of a spectral hair-reader 3110. FIG. 7A is a cross-section view while FIG. 7B is a side view. An illumination source 118 illustrates keratinous fibers, and light (e.g. primarily light of diffusive reflections) therefrom passes through slit or aperture 120. Additional components of the system of FIG. 7A are illustrated in FIGS. 11A-11B, discussed below.

In non-limiting embodiments, the fiber(s) may illuminated by white-light, multi-color light, broadband light, and/or incoherent light.

Figure 8:
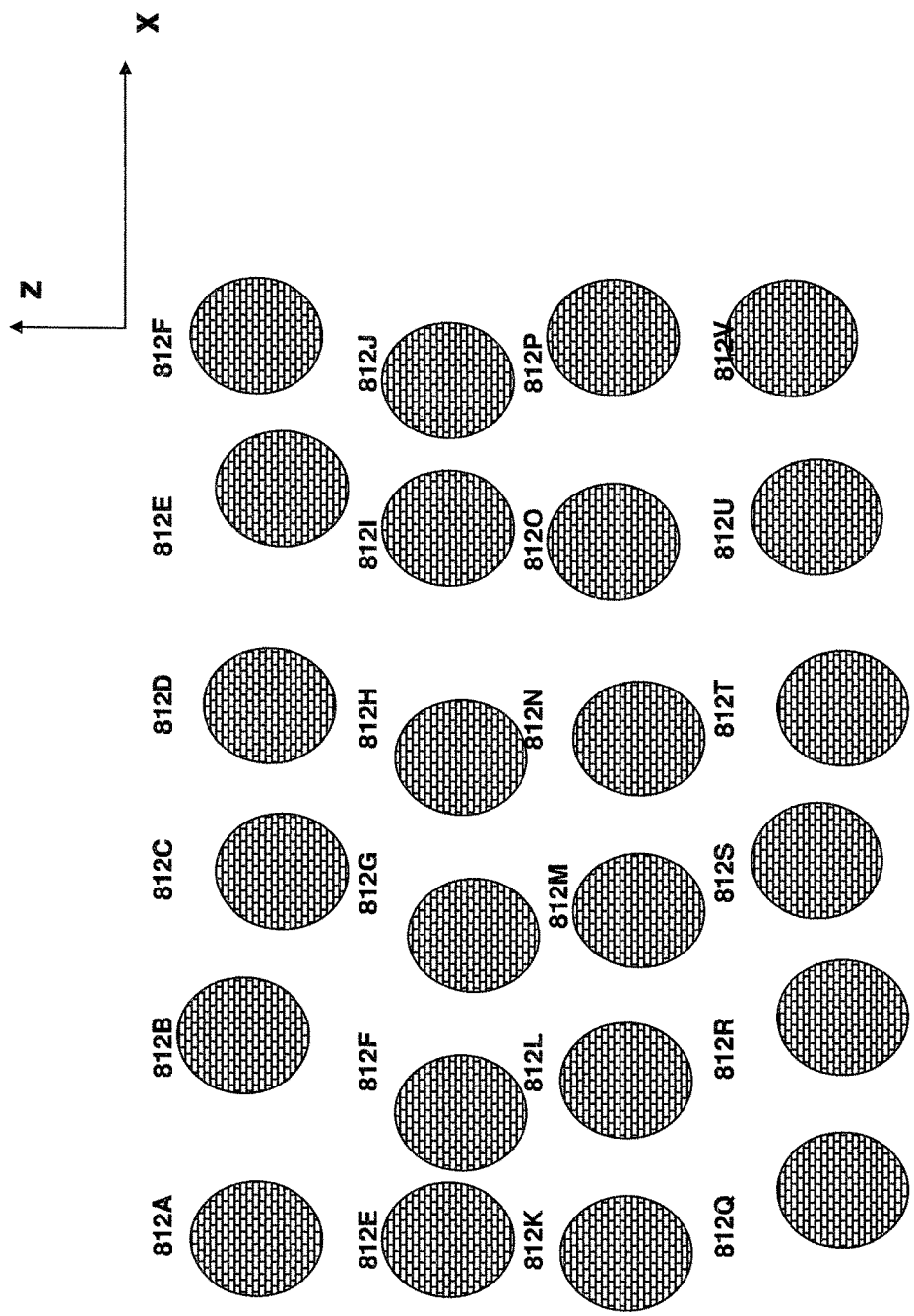

FIG. 8 is a close-up of cross-sectional view of hair shafts 812. Because the hair-shafts are aligned along alignment axis "y", the hair-shafts define two 'lateral axes' perpendicular to alignment axis y—the x axis and the z axis, both of which are illustrated in FIG. 8.

Figure 9:
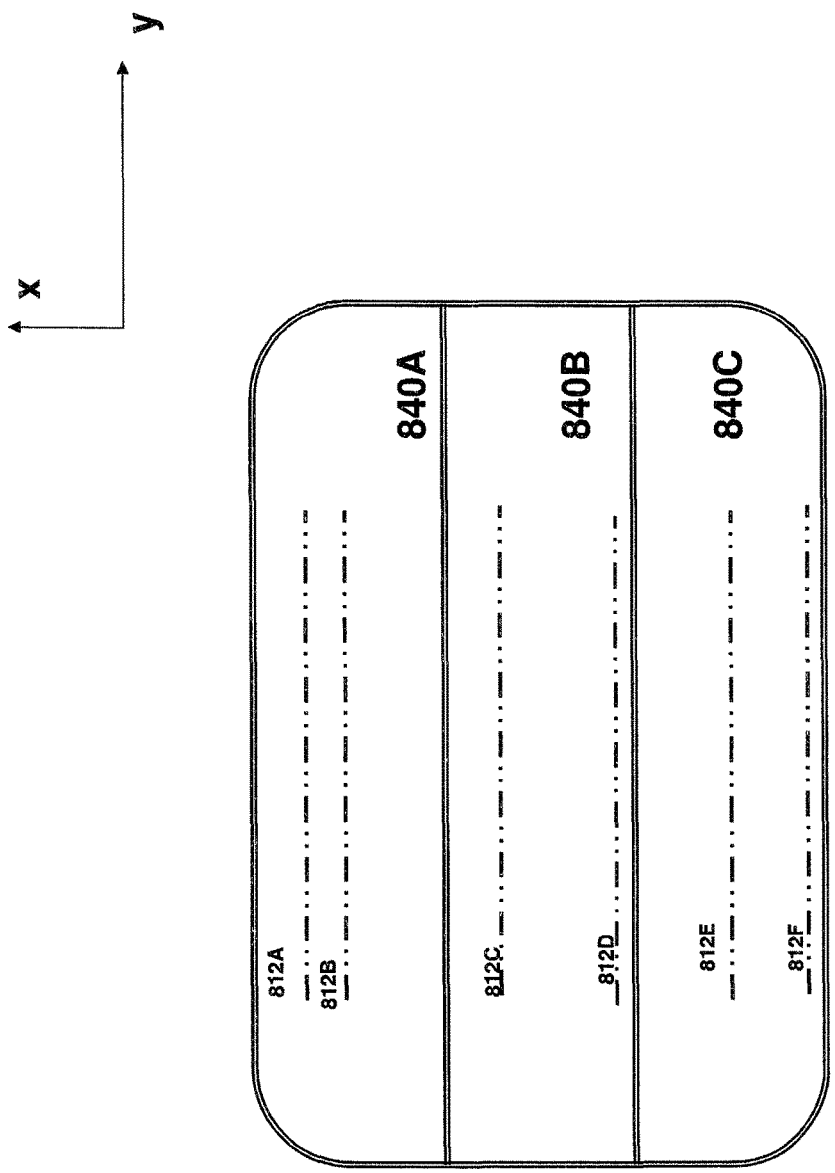

FIG. 9 is a close-up of the top view of hair-shafts of FIG. 6. As shown in FIG. 9, a region in which the hair-shafts are disposed may be divided into 3 portions or slices: (i) slice 840A in which shafts 812A, 812B are disposed; (ii) slice 840B in which shafts 812C, 812D are disposed; and (iii) slice 840C in which shafts 812E, 812F are disposed.

The non-limiting example of FIG. 9 shows a relatively 'simple' case where each slice includes the same number of hair shafts, and every hair-shaft is contained within a single respective slice (i.e. there are no hair-shafts that are partly disposed in multiple slices). The skilled artisan will appreciate that this is not a limitation.

Embodiments of the invention relate to an apparatus whereby instead of measuring a single spectrum (e.g. reflection and/or absorption and/or transmission spectrum) for all hair-shafts, it is possible to measure a different respective spectrum for each slice or sub-region—e.g. a first spectrum for hair shaft(s) disposed within slice 840A, a second spectrum for hair shaft(s) disposed within slice 840B, and a third spectrum for hair shaft(s) disposed within slice 840C.

FIG. 10 illustrates one application of this presently disclosed hair-spectrum-related technique. Case 1 relates to a first hair-type—what may be termed as 'natural grey.' According to Case 1, (i) the following hair-shafts are white-shafts 812A, 812C, and 812D; and (ii) the following hair-shafts are black-shafts 812B, 812E, and 812F. Case 2 relates to a second hair-type—what, may be termed 'artificial grey'—where all hair-shafts have been colored by artificial colorant. Clearly, in Case 2 the hair-shaft color has a greater degree of homogeneity than in Case 1.

Embodiment of the present invention relate to a situation where instead of measuring a single hair-spectrum descriptive of some sort of average of all illuminated hair-shafts, it is possible to determine, for each slice selected from a plurality of slices, a respective hair-spectrum. In Case 1 of FIG. 10, it may be possible to observe significant differences between the respective hair-spectrum for each slice—the spectrum corresponding to slice 840C may be a 'dark-hair' spectrum, the spectrum corresponding to slice 840B may be a 'white-hair' spectrum, and the spectrum corresponding to slice 840A may be a 'grey-hair' spectrum In contrast, in Case 2 of FIG. 10, all three spectra may be quite similar.

In some embodiments, it is thus possible to (i) compare multiple spectra with each other, each spectrum corresponding to a different respective slice 840, and to compute a degree of similarity therebetween and (ii) in accordance with the measured degree of similarity (or difference), distinguish between 'Case 1' and 'Case 2'—in Case 2, a greater degree of similarity between slice-specific hair-spectra may be observed.

FIG. 11A is an non-limiting example of an apparatus for measuring a plurality of spectra of hair-shafts, each spectrum corresponding to a different respective slice in which a different respective set of hair-shafts (or portions thereof) are disposed. One salient feature of FIG. 11A is the presence of two imaging system 1080 and 1070, each of which comprises a different respective set of optical component(s).

Figure 12:
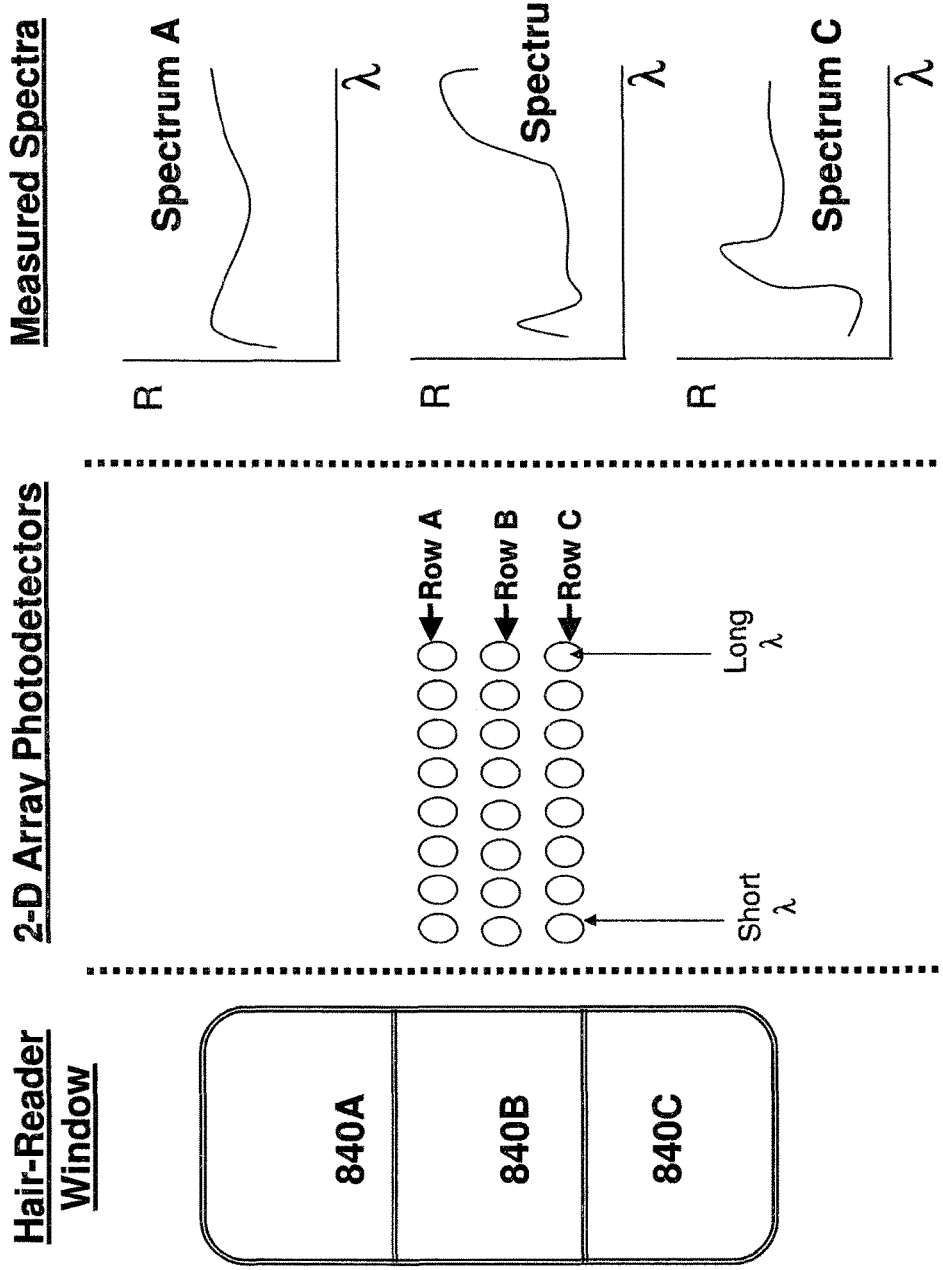

In one non-limiting example, illustrated in FIG. 12, detector 180 comprises an array (e.g. two-dimensional—for example, planar array) of photodetector—in the example of FIG. 12, this is an 8×3 array, though any other section of dimensions (e.g. comprising at least 2 rows and at least 2 columns) may be used. For example, a CCD or CMOS array may be employed.

In some embodiments, imaging system 1080 is operative to focus light reflected and/or deflected and/or transmitted from hair-shafts 812 before this reflected and/or deflected and/or transmitted light passes through slit or aperture 120 so that (i) the hair-shafts 812 are located in an object-plane and (ii) slit or aperture 120 is located in an image plane. In this non-limiting embodiment, the image located at 'image' plane is an 'intermediate image.' The 'intermediate image' (e.g. at slit or aperture 120) may be an only-1D-focused-image—for example, a focused in a dimension perpendicular to hair-alignment axis 812—for example, along the x-axis (see 992 of FIG. 6).

In some embodiments, imaging system 1070 is operative to focus light reflected and/or deflected and/or transmitted from the hair-shafts after passing through slit 120 so that the hair slit 120 (or another 'intermediate' location where the intermediate image) is in an object plane and photodetectors 180 (e.g. a planar two-dimensional array thereof—e.g. a CCD or CMOS array) are in an image plane 180—thus, photodetectors 180 receive an image of slit 120 on which an image of hair-shafts 812 is present—an 'image of an 'image.'

Alternatively, instead of a two-dimensional array of photodetectors (i.e. a 'starting' system), a scanning system may be employed—e.g. to achieve the effect of detecting a two-dimensional image at a focal plane of imaging system 1070.

The image is not required to be located exactly on slit or aperture 120. In and may be located on any location another intermediate location along the optical path between Also illustrated in FIG. 11 is grating 150. Alternatively, a prism may be used.

In another example, it is possible to detect reflection spectrum(a) and/or absorption spectrum(a) and/or transmission spectrum(a) using photodetector that have wavelength and/or 'color' (i.e. in the visible range or any other spectrum) sensitivity.

Similarly, there is no requirement of a slit or elongated aperture—other optical component(s) (e.g. lens(es)) may be configured to provide this functionality.

Thus, some embodiments relate to any device (e.g. monochromator device) configured to measure spectral data (e.g. a reflection, absorption or transmission spectrum) of the keratinous fiber(s).

As illustrated in the non-limiting example of FIG. 12, (i) Row A of the 2D-array of photodetectors 180 is used to detect spectral data of keratinous fiber(s) within slice 840A; (ii) Row B of the 2D-array of photodetectors 180 is used to detect spectral data of keratinous fiber(s) within slice 840B; (iii) Row C of the 2D-array of photodetectors 180 is used to detect spectral data of keratinous fiber(s) within slice 840C. Examples of such spectrum are illustrated in the right-hand column of FIG. 12.

Figure 13:
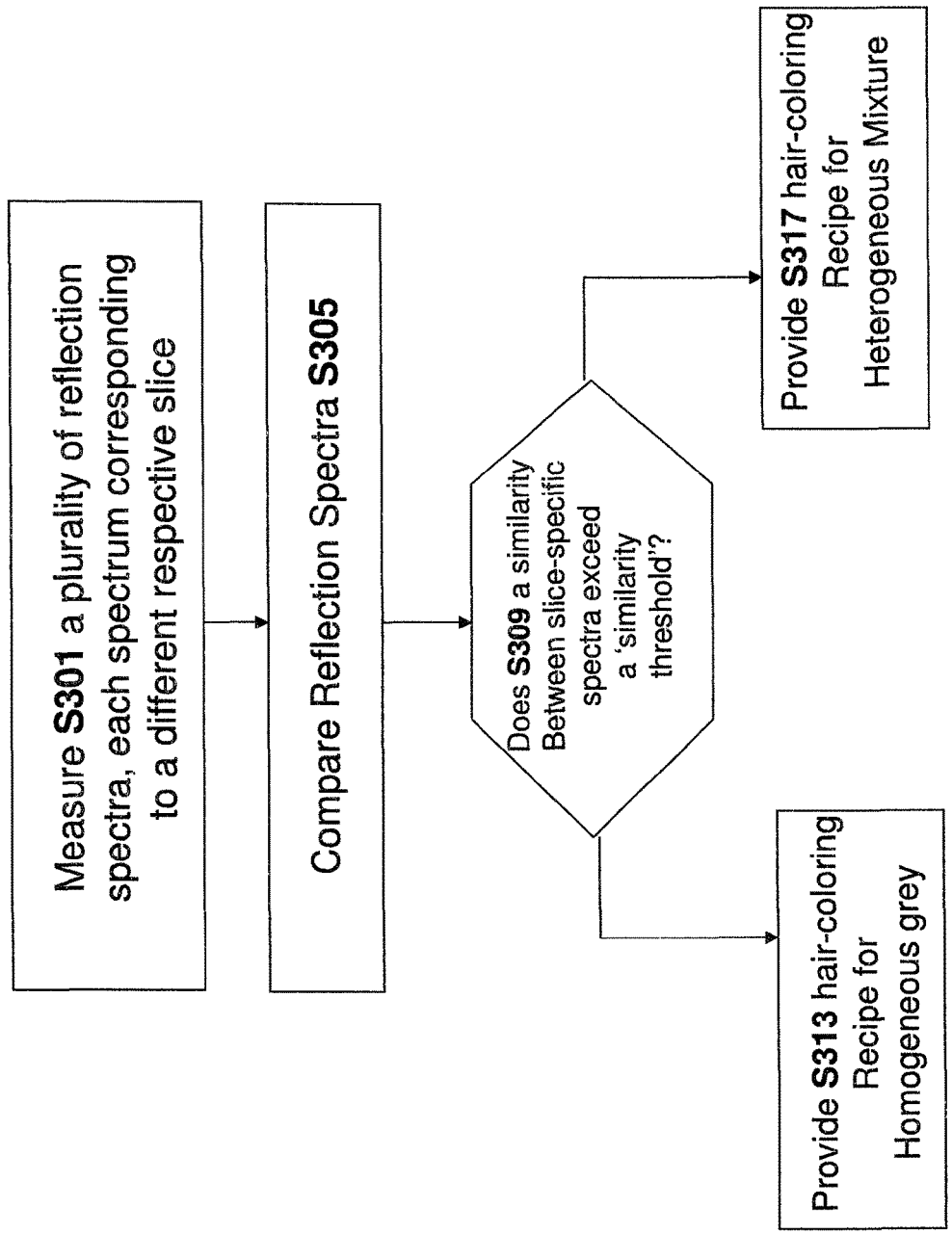

FIG. 13 is a flow chart of a technique for computing a hair-coloring recipe and/or for dispensing hair-coloring agents (e.g. from the dispenser of FIG. 3). In step S301, a plurality of reflection spectra are measured, each spectrum corresponding to a different respective slice—e.g. a first spectrum that is specific to hair shaft(s) within slice 840A, a second spectrum that is specific to hair shaft(s) within slice 840B, and a third spectrum that is specific to hair shaft(s) within slice 840C.

In step S309, the slice-specific spectra are compared with each other, and a parameter descriptive of similarity of multiple spectra may be computed. For example, if the spectra are relatively similar to each other, a recipe S313 may be provided for 'homogenous grey' (see Case 2 of FIG. 10). Alternatively, if the spectra are less similar to each other, a recipe specific to a heterogeneous mixture of hair (see Case 1 of FIG. 10) may be provided. Hair-coloring agents may be dispensed according to the computed hair-coloring recipes.

A Discussion of FIGS. 14-15

Embodiments of the present disclosure relate to apparatus and methods for dispensing "dye couplers" and "dye precursors." In some embodiments and with reference to FIG. 14A, a system 270 for preparing a hair-coloring composition thereof comprises: a. a plurality of containers 280, each container 280 holding therein a different permanent hair color-imparting agent therein and b. a dispenser configured to dispense the contents of the containers thereof to provide multi-container combinations of hair-coloring agents or ingredients.

In some embodiments, the contents of a first of the plurality of containers (e.g. container 280A) comprise dye precursor and is substantially free of dye coupler. When a contents of a container "comprise dye precursors" and are "substantially free" of dye-coupler, this means that either (i) the contents comprise only dye precursor and are free of dye-coupler or that (ii) a dye precursor:dye coupler weight ratio of the contents of the containers is at least 1.5:1 or at least 2:1 or at least 3:1 or at least 5:1, at least 10:1, at least 50:1, at least 100:1, at least 500:1, at least 1000:1, at least 5000:1, or at least 10,000:1.

As noted above, in some embodiments, in some embodiments, the contents of a first of the plurality of containers (e.g. container 280A) comprise dye precursor and is substantially free of dye coupler. Alternatively or additionally, contents of a second of the containers (e.g. container 280B) comprise dye coupler and is substantially free of dye precursor. When a contents of a container "comprise dye precursor coupler" and are "substantially free" of dye-precursor, this means that either (i) the contents comprise only dye coupler and are free of dye-precursor or that (ii) a dye coupler: dye precursor weight ratio of the contents of the containers is at least 1.5:1 or at least 2:1 or at least 3:1 or at least 5:1, at least 10:1, at least 50:1, at least 100:1, at least 500:1, at least 1000:1, at least 5000:1, or at least 10,000:1.

As discussed below, in some embodiments, the dispenser is automatic and may automatically dispense contents of the containers 280 to provide the multi-container combination—for example, in accordance with at least one of (i) a hair coloring target and/or (ii) hair spectroscopy data. Alternatively, the dispenser may be a manually operated.

Not wishing to be bound by theory, the present inventors have found that for multi-container devices that dispense color-imparting agents, that there may be more than 'path' or method for achieving a certain target hair-color composition. For example, to achieve a hair-coloring composition HCC with specific properties, it may be possible to either (i) dispose a quantity QA1 of color-imparting agent CIA_A from Container A 280A, a quantity QC1 of color-imparting agent CIA_C from Container C 280C and a quantity QG1 of color-imparting agent CIA_G from Container G 280G and to mix these color imparting agents together OR (ii) dispose a quantity QD1 of color-imparting agent CIA_D from Container D 280D, and a quantity QE1 of color-imparting agent CIA_E from Container E 280E. The present inventors have found, however, that by segregating dye precursors from dye couplers, it is possible to increase the number of 'paths' or coloring-agent compositions available to achieve (i.e. by mixing) the provision of certain hair-colors.

During use of dispenser 270, the hair-coloring agents in the different containers may be used up and require replacement at different times—e.g. not all containers exhaust their supply of hair-coloring agent simultaneously. If, however, it is possible to achieve various color combinations without require on a presence of color-imparting agent within a 'particular container,' the user can continue using the dispenser even when the containers of the 'particular container' are exhausted, as long as alternative combinations of 'paths' of achieving the various color combinations are available only using the contents of the other containers (i.e. other than the 'particular container').

By implementing a system which, in general, increases the number of available 'paths' or 'mixing combinations' (i.e. by means of segregation of precursor and coupler), it is possible for a user of dispenser 270 to operate the dispenser with less of a need to immediately refill containers whose contents have been exhausted.

For cases where the dispenser 270 is automatic, dispenser 270 may include any combination of mechanical and/or electric components needed to dispense hair color-imparting agents.

FIG. 14A is a schematic diagram of a system 270 for dispensing agents related to permanent hair-coloring into target vessel 290. The agents are stored in containers 280—in the non-limiting example of FIG. 1A, the system includes 7 container 280A-280G. Within each container is stored respective hair-coloring agent, for example, related to permanent hair-coloring.

Operation of lever 284 dispenses material from the containers into a target vessel 292 located within port 288. The material may be dispensed sequentially or simultaneously. In FIG. 14B, material from container C 280C is dispensed into vessel 292. In FIG. 14C, material from container E 280E is dispensed into vessel 292.

Dispensing system is thus configured to dispense color-imparting agents from a any subset of the plurality of containers to provide any multi-container combination.

The quantities of color-imparting agent disposed from each container 280 may be determined manually or automatically. In one embodiment, the quantities are computed in accordance with at least one of (i) a hair coloring target and/or (ii) hair spectroscopy data.

Within the containers, the coloring agents may be provided as solid material (e.g. for example, as tablets or as particulate matter such as powders), as a liquid, cream, gel, emulsion, or in any other phase or combination thereof. The coloring agents in each container does not need to be in the same phase. This applies to any container including but not limited to (i) the container comprising dye precursor and substantially free of dye-coupler and/or (ii) the container comprising—i.e. the contents of any such container may be solid material (e.g. for example, as tablets or as particulate matter such as powders), as a liquid, cream, gel, emulsion, or in any other phase or combination thereof.

In a first non-limiting example, (i) the coloring agent within first container 280A comprise dye precursors and is substantially free of dye-coupler, (ii) the coloring agent within second container 280B comprise dye coupler and is substantially free of dye-precursor, (iii) the respective coloring agent within each of the first 280A and second 280B containers is provided as a solid material—for example, in tablet form.

In a second non-limiting example, (i) the coloring agent within first container 280A comprise dye precursors and is substantially free of dye-coupler, (ii) the coloring agent within second container 280B comprise dye coupler and is substantially free of dye-precursor, (iii) the respective coloring agent within each of the first 280A and second 280B containers is provided as liquid or gel or mousse.

In a third non-limiting example, (i) the coloring agent within first container 280A comprise dye precursors and is substantially free of dye-coupler, (ii) the coloring agent within second container 280B comprise dye coupler and is substantially free of dye-precursor, (iii) the coloring agent within the first 280A container is provided as a solid material (e.g. in tablet format) and the coloring agent within the first 280A container is provided as a liquid.

Embodiments where one or more of the containers contains one or more tablets including a hair color-imparting agent are now discussed.

In some of the embodiments related to tablets, one or more (e.g. at least 1, at least 2, at least 5, or least 10, or at least 25, or at least 50, or at least 100) tablets are disposed in the first container 280A are such that for each tablet, the ratio by weight of dye precursor to coupler is at least 1.5:1 or at least 2:1 or at least 3:1 or at least 5:1, at least 10:1, at least 50:1, at least 100:1, at least 500:1, at least 1000:1, at least 5000:1, or at least 10,000:1 or infinity (e.g. denominator has a value of zero so ratio is undefined or approaches or is infinity).

In some embodiments, (i) in a first 280A of the containers, a majority or a substantial majority of all tablets disposed therein are such that a ratio by weight of coupler to dye precursor in the container is at least 1.5:1 or at least 2:1 or at least 3:1 or at least 5:1, at least 10:1, at least 50:1, at least 100:1, at least 500:1, at least 1000:1, at least 5000:1, or at least 10,000:1 or infinity (e.g. denominator has a value of zero so ratio is undefined or approaches or is infinity); and (ii) in a second 280B of the containers, a majority or a substantial majority of all tablets disposed therein are such a ratio by weight of dye precursor to coupler in the container is at least 1.5:1 or at least 2:1 or at least 3:1 or at least 5:1, at least 10:1, at least 50:1, at least 100:1, at least 500:1, at least 1000:1, at least 5000:1, or at least 10,000:1 or infinity (e.g. denominator has a value of zero so ratio is undefined or approaches or is infinity).

In any container there may any number of tablets—for example, at least 1, at least 2, at least 5, or at least 10, or at least 25, or at least 50, or at least 100.

Embodiments related to different 'loads' are now discussed. Tablets of the 'first type' comprise dye precursor and are substantially free of dye coupler, that tablets of the 'second type' comprise dye coupler and are substantially free of dye precursor.

The term 'load of a tablet' comprising color-imparting agent relates to the weight or moles of the active hair-coloring ingredient.

For a tablet of the 'first type,' a 'load by weight' is the weight (e.g. in grams) of dye precursor within the tablet. For a tablet of the 'second type,' a 'load by weight' is the weight (e.g. in grams) of dye coupler within the tablet. For a tablet of the 'second type,' a 'load by moles' is the number of moles of dye precursor within the tablet. For a tablet of the 'second type,' a 'load by moles' is the number of moles of dye coupler within the tablet.

In some embodiments, (i) each of at least majority of (or each of at least a substantial majority of or all) tablets in the first container 280A are of a first type and/or (ii) each of at least majority of (or each of at least a substantial majority of or all) of tablets in the second container 280B are of a second type and/or (iii) each of at least majority of (or each of at least a substantial majority of or) tablets in the third container 280C are of the first type; and/or (iv) each of at least majority of (or each of at least a substantial majority of or) tablets in the fourth container 280D are of the second type.

According to a first example, the same dye precursor is stored in the first 280A and third container 280C, however, at different loads. Thus, in the first example, it is possible to compare loads or volumes between (i) a set TABLET_SET1 of tablets within the first container 280A and (ii) a set TABLET_SET3 of tablets within the third container 280C where all tablets of TABLET_SET1 and all tablets of TABLET_SET3 are of the 'first type' and comprise the same dye precursor and are all substantially free of dye coupler. In this first example, at least a majority or at least a substantial majority or all tablets stored within the first 280A container are members of set TABLET_SET1; at least a majority or at least a substantial majority or all tablets stored within the third 280C container are members of set TABLET_SET3. In this first example, an average volume of tablets of set TABLET_SET1 is $VOL_1$ and an average load (by mole) of tablets of set TABLET_SET1 is $LM_1$ and average load (by weight) of tablets of set TABLET_SET1 is $LW_1$. For example, all tablets of TABLET_SET1 may have the same volume or load by weight or load by mole. In this first example, an average volume of tablets of set TABLET_SET3 is $VOL_3$ and an average load (by mole) of tablets of set TABLET_SET3 is $LM_3$ and average load (by weight) of tablets of set TABLET_SET3 is $LW_3$. For example, all tablets of TABLET_SET1 may have the same volume or the same load (by weight) or the same load (by mole). Alternatively or additionally, all tablets of TABLET_SET3 may have the same volume or the same load (by weight) or the same load (by mole).

According to this first example, at least one or at least two or at least three of the following is true: (i) load-weight ratio $LW_1/LW_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 101 and/or (ii) load-molar ratio $LM_1/LM_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 101 and/or a (ii) volume ratio $VOL_1/VOL_3$ is at least 1.1 or at least 1.2 or at least 1.25 or at least 1.3 or at least 1.4 or at least 1.5 or at least 1.75 or at least 2 or at least 3 or at least 5 or at least 7.5 or at least 10.

Alternatively or additionally, according to a second example, the same dye coupler is stored in the second 280B and fourth container 280D, however, at different loads. Thus, in the second example, it is possible to compare loads or volumes between (i) a set TABLET_SET2 of tablets within the second container 280B and (ii) a set TABLET_SET4 of tablets within the fourth container 280D where all tablets of TABLET_SET2 and all tablets of TABLET_SET4 are of the 'second type' and comprise the same dye coupler and are all substantially free of dye precursor. In this second example, at least a majority or at least a substantial majority or all tablets stored within the second 280B container are members of set TABLET_SET12, at least a majority or at least a substantial majority or all tablets stored within the fourth 280D container are members of set TABLET_SET4. In this second example, an average volume of tablets of set TABLET_SET2 is $VOL_2$ and an average load (by mole) of tablets of set TABLET_SET2 is $LM_2$ and average load (by weight) of tablets of set TABLET_SET2 is $LW_2$. For example, all tablets of TABLET_SET2 may have the same volume or load by weight or load by mole. In this second example, an average volume of tablets of set TABLET_SET4 is $VOL_4$ and an average load (by mole) of tablets of set TABLET_SET4 is $LM_4$ and average load (by weight) of tablets of set TABLET_SET4 is $LW_4$. For example, all tablets of TABLET_SET2 may have the same volume or the same load (by weight) or the same load (by mole). Alternatively or additionally, all tablets of TABLET_SET4 may have the same volume or the same load (by weight) or the same load (by mole).

According to this first example, at least one or at least two or at least three of the following is true: (i) load-weight ratio $LW_2/LW_4$ is at least 1.1 or at least 1.2 or at least 1.25 or at least 1.3 or at least 1.4 or at least 1.5 or at least 1.75 or at least 2 or at least 3 or at least 5 or at least 7.5 or at least 101 and/or (ii) load-molar ratio $LM_2/LM_4$ is at least 1.1 or at least 1.2 or at least 1.25 or at least 1.3 or at least 1.4 or at least 1.5 or at least 1.75 or at least 2 or at least 3 or at least 5 or at least 7.5 or at least 101 and/or a (ii) volume ratio $VOL_2/VOL_4$ is at least 1.1 or at least 1.2 or at least 1.25 or at least 1.3 or at least 1.4 or at least 1.5 or at least 1.75 or at least 2 or at least 3 or at least 5 or at least 7.5 or at least 10.

Embodiments of the invention relate to the dispensing of a "multi-container tablet combination" from a plurality of tablets. This means that for a plurality of N containers $Container_1 \ldots Container_N$ (where N is a positive integer equal to at least 2), for two positive integers i and j ($i \neq j$, both i and j are equal to at least 1 and at most N), at least one tablet (in some embodiments, a plurality of tablets) is dispensed from $Container_i$ and at least one tablet (in some embodiments, a plurality of tablets) is dispensed from $Container_j$.

In some embodiments, when a tablet dispenser dispenses tablets a tablet "in accordance with one or more properties" (e.g. a hair coloring target and/or hair spectroscopy data), the quantity of tablets (i.e. number and/or volume and/or weight—for example, relative quantities of tablets from multiple containers where different types of tablets are stored in each container) is determined according to the properties—for example, by electronic circuitry—for example, according to some algorithm predicting an outcome of a hair coloring.

In some embodiments, a liquid dispenser may dispense a flowable medium (e.g. a liquid or cream or gel or emulsion) "in accordance with one or more properties" (e.g. a hair coloring target and/or hair spectroscopy data)—this may refer to the quantity of flowable medium—for example, absolute quantities or relative quantities of flowable medium relative to tablets or relative quantities of one flowable medium (i.e. in a first reservoir) relative to another flowable medium (i.e. in a second reservoir). This may, for example, be carried out to dilute a flowable medium of one of the reservoirs with that or another reservoir. The determining may be carried out for example, by electronic circuitry—for example, according to some algorithm predicting an outcome of a hair coloring.

An example of a 'reservoir' is illustrated in FIG. 15.

A Discussion of FIGS. 16-19

FIGS. 16-19 relate to dispensing of cosmetic agents (e.g. for hair-coloring or for any other cosmetic application) where for each container, data describing physical and/or chemical property(ies) of the cosmetic material therein is encoded on the container.

Within each container is stored a cosmetic agent—for example, a hair-coloring agent or any other cosmetic agent known (e.g. for applications other than hair-coloring) in the art.

On each container 180A-180P (e.g. mounted thereon or therein, embedded in the container) is a different respective data-storage element 190A-190B for storing information about the contents of each container. Examples of data-storage elements include but are not limited to hologram elements, barcodes, QR codes, I2C EEPROM, magnetic coding elements, mechanical coding elements and RFID elements.

This data-storage element may be read by a code-reader 188—e.g. operatively linked to the dispenser and/or to an electronic controller thereof.

In different embodiments, one or more the following data-items about the contents of the containers may be encoded: batch number, material type in the container, quantity data (e.g. the initial quantity or current quantity within the container), material version, dyes content (e.g. for the colorants), production date, levels of ammonia, peroxide, MEA, viscosity (e.g. for the creams), and expiration date.

In yet another example, use-history and/or storage-history data related to the container or contents thereof may be stored. In one example, it may be possible to store a time or date when the container is installed onto the dispenser. Alternatively or additionally, it may be possible to store a temperature and/or humidity history of the ambient environment in which the container is situated—e.g. to compute the effect of 'aging' upon the material within the containers. In some embodiments, code-reader 188 may be operative to write (or otherwise update) data to data-storage element 190.

Not every cosmetic agent may age in the same manner—thus, it is possible that a first cosmetic agent loses its potency at a faster rate than a second agent. In this situation, the algorithm for computing the relative quantities of cosmetic agent required for a cosmetic objective (e.g. hair-coloring) may be influenced by the age (i.e. chronological age or another method of aging of the material—e.g. material stored in a high humidity environment may age differently than material stored in a low material environment). This is discussed below with reference to FIG. 19.

Reference is made to FIG. 17A. In step S701, the code is read by code-reader 188 from data-storage element 190. In step S705, the contents are dispensed according to the results of code-reading.

One application is to make sure that only safe and cosmetically-acceptable material is dispensed from the containers. Thus, in step S711 of FIG. 17B, a container is only 'eligible' (step S715) or dispensing if the material meets this standard. Otherwise (step S719) the dispenser may refuse to dispense material containing unacceptable material.

In some embodiments, the results of the code-reading (step S701 by code-reader 188) may the behavior of dispensing decision engine 3140—e.g. by influence predicting and/or scoring of a candidate recipe. In one example, different batches may having slightly different but not identical physical and/or chemical property(ies). In another example, as material ages its physical and/or chemical property(ies) change. Thus, a recipe using the recently-manufactured material may have a different effect on a user's hair than the same receipt using the same material after aging.

Figure 18:
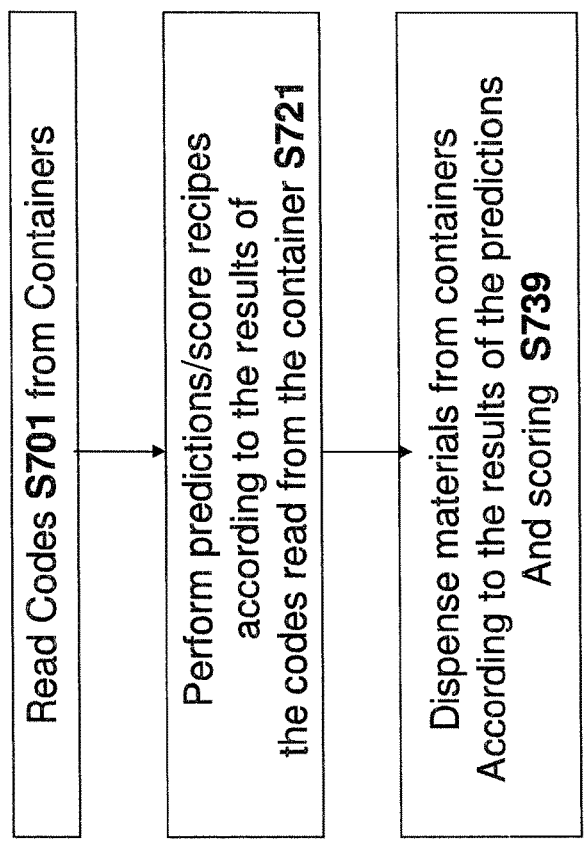

FIG. 18 relates to the situation where the results of the code reading influence the behavior of dispensing decision engine 3140. In step S721, the predictions of the influence of recipes upon a user's hair and/or the scoring of a particular recipe may be performed according to the results of the code-reading, and the materials are dispensed from the containers (in step S739) according to the influenced scoring/predicting.

Figure 19:
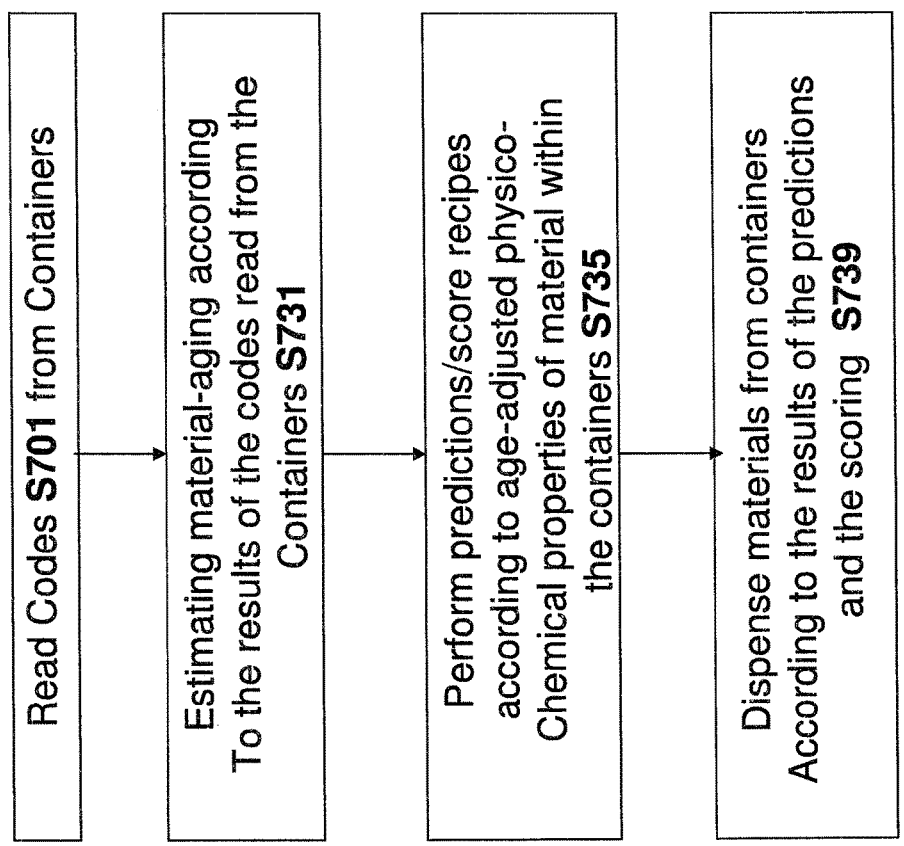

FIG. 19 is a method for dispensing material from containers according to a material-aging property computed from data read from data-storage element 190.

It is possible to store in data-storage element both (i) reference or baseline physical and/or chemical property(ies) of the cosmetic agent (e.g. their properties upon manufacture or upon opening of the container or upon engaging the container to the dispenser) and (ii) a material aging-metric—the amount of time since the baseline properties prevailed, or other history data related to aging—e.g. humidity or temperature over time.

When there is a need to dispense different relative quantities of material from the dispensers, it is possible to compute from the base-line properties and from the aging metric an estimate of current physical and/or chemical property(ies) of material within the container (step S731 of FIG. 19). From this estimate, it is possible to dispense the appropriate quantity. For example, this estimate may be used (i.e. in steps S735-S739 of FIG. 19) to use as input to any algorithm for dispensing material described herein.

Thus, some embodiments relate to a system for dispensing cosmetic ingredients comprising: a. a dispensing device; b. a plurality of containers, each containing a different respective cosmetic agent stored therein having different respective cosmetic properties, each container encoded with respective data describing both (i) reference physical-chemical property(ies) of the cosmetic agent stored therein and (ii) an ageing metric describing an extent of aging of the cosmetic material; and c. a code-reader included in or operatively linked to the dispensing device, the code-reader being configured to read the respective encoded reference physical-chemical property(ies) and ageing metrics from each of the containers, wherein: i. the dispensing device is configured, when the containers are engaged thereto, to dispense cosmetic agents from the containers in relative quantities determined in accordance with estimations of current physical-chemical property(ies) of the cosmetic agents stored within the containers; and ii. the estimations of current physical-chemical properties of each cosmetic agent are computed in accordance with both (i) reference physical-chemical property(ies) of the cosmetic agent stored therein and (ii) an ageing metric describing an extent of aging of the cosmetic material Examples of ageing metrics include (i) an amount of elapsed time since manufacture or opening the container or engagement of the container to the dispenser; and (ii) historical temperature or humidity.

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. A system for preparing a hair-coloring composition, the system comprising:
   a dispenser configured to dispense keratinous fiber treatment tablets from at least a first keratinous fiber treatment tablet container and a second keratinous fiber treatment tablet container;
   the first keratinous fiber treatment tablet container having tablets including a permanent hair-coloring dye precursor and that are substantially free of permanent hair-coloring dye coupler;
   the second first keratinous fiber treatment tablet container having tablets including a permanent hair-coloring dye coupler and that are substantially free of permanent hair-coloring dye precursor; and
   the dispenser configured to provide multi-container keratinous fiber treatment tablet combinations,
   wherein at least a majority of the tablets in the first container comprise substantially the same dye coupler and have substantially the same size, and
   wherein the plurality of containers comprises a third container having tablets, such that (i) at least a majority of the tablets within the first container are members of TABLET_SET1; (ii) at least a majority of the tablets within the third container are members of TABLET_SET3; (iii) all the tablets of TABLET_SET1 are of a first type and comprise the same precursor PREC_1; (iv) all the tablets of TABLET_SET3 are of the first type and comprise the same precursor PREC_1 that is the same as that of TABLET_SET3; (v) an average load (by weight) of the tablets of TABLET_SET1 is $LW_1$; (vi) an average load (by weight) of the tablets of TABLET_SET3 is $LW_3$; and (vii) and a ratio between $LW_1$ and $LW_3$ is at least 1.25.

2. The system of claim 1, wherein the dispenser is configured to dispense the multi-container combinations in accordance with at least one of (i) a hair coloring target and/or (ii) hair spectroscopy data.

3. The system of claim 1, further comprising:
   electronic circuitry to compute the multi-container tablet combinations upon considering initial properties of keratinous fibers, the electronic circuitry controlling the dispenser to provide the multi-container tablet combinations.

4. A system for preparing a hair-coloring composition, the system comprising:
   a dispenser configured to dispense keratinous fiber treatment tablets from at least a first keratinous fiber treatment tablet container and a second keratinous fiber treatment tablet container;
   the first keratinous fiber treatment tablet container having tablets including a permanent hair-coloring dye precursor and that are substantially free of permanent hair-coloring dye coupler;
   the second first keratinous fiber treatment tablet container having tablets including a permanent hair-coloring dye coupler and that are substantially free of permanent hair-coloring dye precursor; and
   the dispenser configured to provide multi-container keratinous fiber treatment tablet combinations,
   wherein at least a majority of the tablets in the first container comprise substantially the same dye coupler and have substantially the same size, and
   wherein the plurality of containers comprises a third container having tablets, such that (i) at least a majority of the tablets within the first container are members of TABLET_SET_1; (ii) at least a majority of the tablets within the third container are members of TABLET_SET3; (iii) all the tablets of TABLET_SET1 are of a first type and comprise the same precursor PREC_1; (iv) all the tablets of TABLET_SET3 are of a first type and comprise the same precursor PREC_1 that is the same as that of TABLET_SET3; (v) an average load (by mole) of the tablets of TABLET_SET1 is $LM_1$; (vi) an average load (by weight) of the tablets of TABLET_SET3 is $LM_3$; and (vii) and a ratio between $LM_1$ and $LM_3$ is at least 1.5.

5. The system of claim 4, wherein the dispenser is configured to dispense the multi-container combinations in accordance with at least one of (i) a hair coloring target and/or (ii) hair spectroscopy data.

6. The system of claim 4, further comprising:
   electronic circuitry to compute the multi-container tablet combinations upon considering initial properties of keratinous fibers, the electronic circuitry controlling the dispenser to provide the multi-container tablet combinations.

7. A system for preparing a hair-coloring composition, the system comprising:
   a dispenser configured to dispense keratinous fiber treatment tablets from at least a first keratinous fiber treatment tablet container and a second keratinous fiber treatment tablet container;
   the first keratinous fiber treatment tablet container having tablets including a permanent hair-coloring dye precursor and that are substantially free of permanent hair-coloring dye coupler;
   the second first keratinous fiber treatment tablet container having tablets including a permanent hair-coloring dye coupler and that are substantially free of permanent hair-coloring dye precursor; and
   the dispenser configured to provide multi-container keratinous fiber treatment tablet combinations,
   wherein at least a majority of the tablets in the first container comprise substantially the same dye coupler and have substantially the same size, and
   wherein the plurality of containers comprises a third container having tablets, such that (i) at least a majority of the tablets within the first container are members of TABLET SET_1; (ii) at least a majority of the tablets within the third container are members of TABLET_SET3; (iii) all the tablets of TABLET_SET1 are of a first type and comprise the same precursor PREC_1; (iv) all the tablets of TABLET_SET3 are of the first type and comprise the same precursor PREC_1 that is the same as that of TABLET_SET3; (v) an average volume of the tablets of TABLET_SET1 is $VOL_1$; (vi) an average volume of the tablets of TABLET_SET3 is $VOL_3$; and (vii) and a ratio between $VOL_1$ and $VOL_3$ is at least 2.

8. The system of claim 7, wherein all the tablets of TABLET_SET_1 have substantially the same volume and/or substantially the same load (by weight) of precursor PREC_1 and/or substantially the same load (by mole) of precursor PREC_1.

9. The system of claim 8, wherein all the tablets of TABLET_SET3 have substantially the same volume and/or substantially the same load (by weight) of precursor PREC_1 and/or substantially the same load (by mole) of precursor PREC_1.

10. The system of claim 7, wherein the dispenser is configured to dispense the multi-container combinations in accordance with at least one of (i) a hair coloring target and/or (ii) hair spectroscopy data.

11. The system of claim 7, further comprising:
electronic circuitry to compute the multi-container tablet combinations upon considering initial properties of keratinous fibers, the electronic circuitry controlling the dispenser to provide the multi-container tablet combinations.

* * * * *